United States Patent [19]
Kline

[11] Patent Number: 5,181,421
[45] Date of Patent: Jan. 26, 1993

[54] AUTOMATIC MONITORING OF COMPOSITE PREPREGS

[75] Inventor: Ronald A. Kline, Norman, Okla.

[73] Assignee: Board of Regents of the University of Oklahoma, Norman, Okla.

[21] Appl. No.: 709,722

[22] Filed: Jun. 3, 1991

Related U.S. Application Data

[63] Continuation of Ser. No. 556,087, Jul. 20, 1990, Pat. No. 5,127,268, and a continuation-in-part of Ser. No. 371,653, Jun. 21, 1989, Pat. No. 5,031,457, which is a continuation of Ser. No. 309,004, Feb. 7, 1989, abandoned, which is a continuation of Ser. No. 147,155, Jan. 22, 1988, abandoned.

[51] Int. Cl.$^5$ .................................... G01N 29/00
[52] U.S. Cl. ................................. 73/597; 73/635
[58] Field of Search ............... 73/597, 598, 599, 602, 73/632, 635, 644

[56] References Cited

U.S. PATENT DOCUMENTS

| | | | |
|---|---|---|---|
| 3,720,098 | 3/1973 | Dixon | 73/597 |
| 3,995,501 | 12/1976 | Wiley | 73/597 |
| 4,735,087 | 4/1988 | Hourani et al. | 73/597 |
| 4,745,809 | 5/1988 | Collins et al. | 73/597 |
| 5,024,091 | 6/1991 | Pellerin et al. | 73/602 |
| 5,031,457 | 7/1991 | Kline | 73/597 |
| 5,074,149 | 12/1991 | Stearns | 73/599 |

OTHER PUBLICATIONS

The Analysis of Fibre-Reinforced Porous Composite Materials by the Measurement of Ultrasonic Wave Velocities—Ultrasonics, Jul. 1978, 5 pages, ©1978 IPC Business Press Ltd.

*Primary Examiner*—Louis Arana
*Attorney, Agent, or Firm*—Dunlap, Codding & Lee

[57] ABSTRACT

A method and apparatus for non-destructively determining fiber volume fraction and resin porosity of a composite material or prepreg wherein the composite material or prepreg is moved between a roller and a roller-transducer housing. A transducer assembly is supported in the roller-transducer housing for propagating two independent acoustic waves through the composite material. A water medium is disposed in the roller-transducer housing. The two acoustic waves are propagated through the water medium, through the thickness of the roller-transducer housing and through the composite material or prepreg. The velocity of each of two acoustic waves, $V_1$ and $V_2$, are determined and the thickness of the composite material or prepreg is determined. The fiber volume fraction in resin porosity of the composite material or prepreg are then determined using the velocities $V_1$ and $V_2$, the thickness and known parameters of density, elastic modulii of the constituent material and layup sequence.

16 Claims, 9 Drawing Sheets

SPECIMEN GEOMETRY

VS vs VL (UNIDIRECTIONAL LAMINATE)

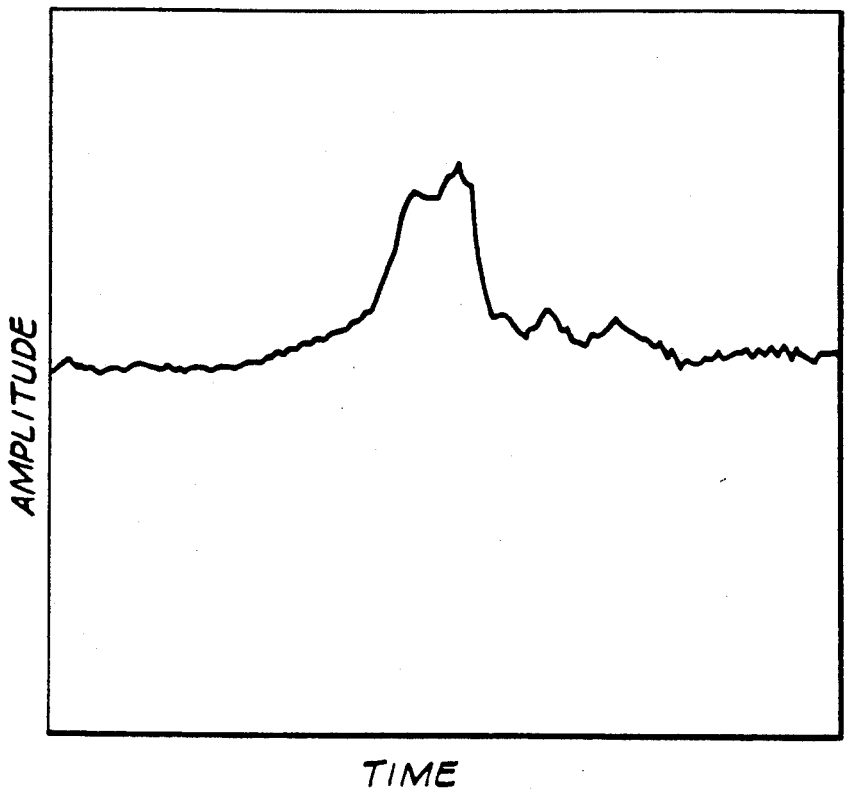
FIG. 12
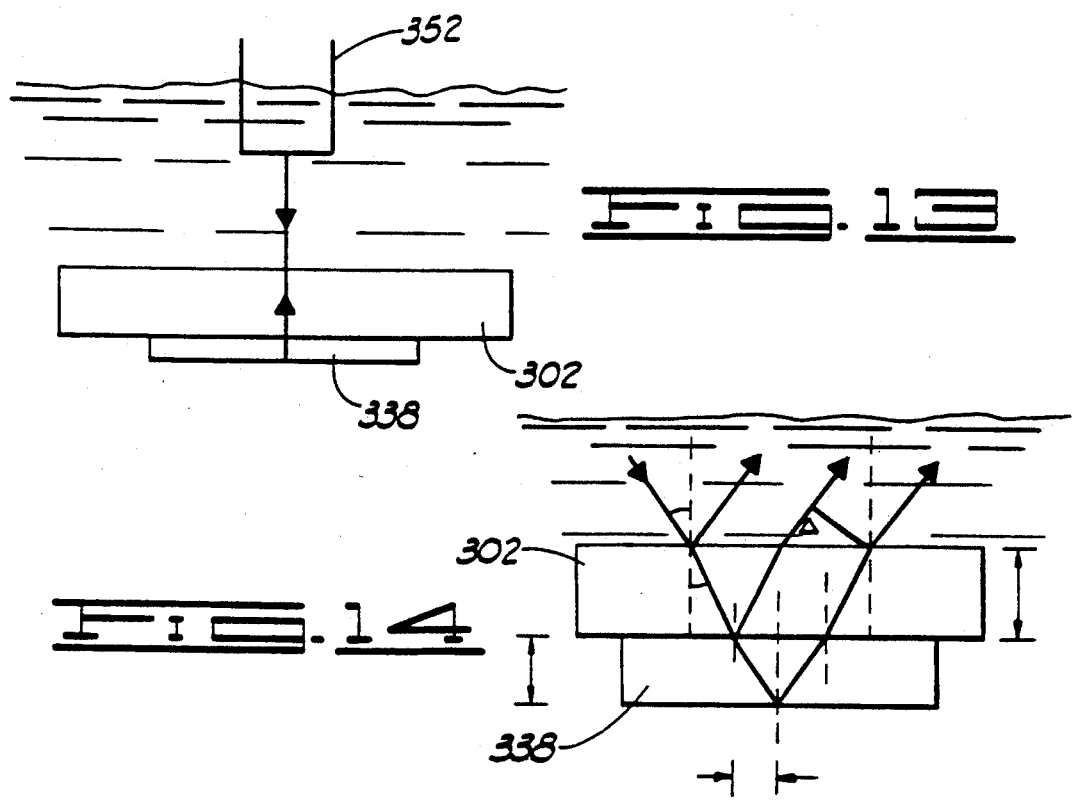
FIG. 13
FIG. 14

AUTOMATIC MONITORING OF COMPOSITE PREPREGS

CROSS REFERENCE TO RELATED APPLICATIONS

This application is a continuation of U.S. Ser. No. 556,087, filed Jul. 20, 1990, now U.S. Pat. No. 5,127,268. This application also is a continuation-in-part of U.S. Ser. No. 371,653, filed Jun. 21, 1989, now U.S. Pat. No. 5,031,457, which was a continuation of U.S. Ser. No. 309,004, filed Feb. 7, 1989, now abandoned, which was a continuation of U.S. Ser. No. 147,155, filed Jan. 22, 1988, now abandoned.

FIELD OF THE INVENTION

The present invention relates generally to systems for determining parameters of materials and, more particularly, but not by way of limitation to systems for nondestructive determining fiber volume fraction and resin porosity of composite materials constructed of at least two different constituent materials.

BRIEF DESCRIPTION OF THE DRAWINGS

FIG. 12 is a graphical representation of the analytical signal magnitude of a shear wave.

FIG. 13 is a schematic representation of longitudinal wave propagation through a water medium from a longitudinal transducer through a section of a roller and through prepreg.

FIG. 14 is a schematic representation of shear wave propagation through a water medium, a roller and prepreg.

DESCRIPTION OF THE PREFERRED EMBODIMENTS

Figure 1:
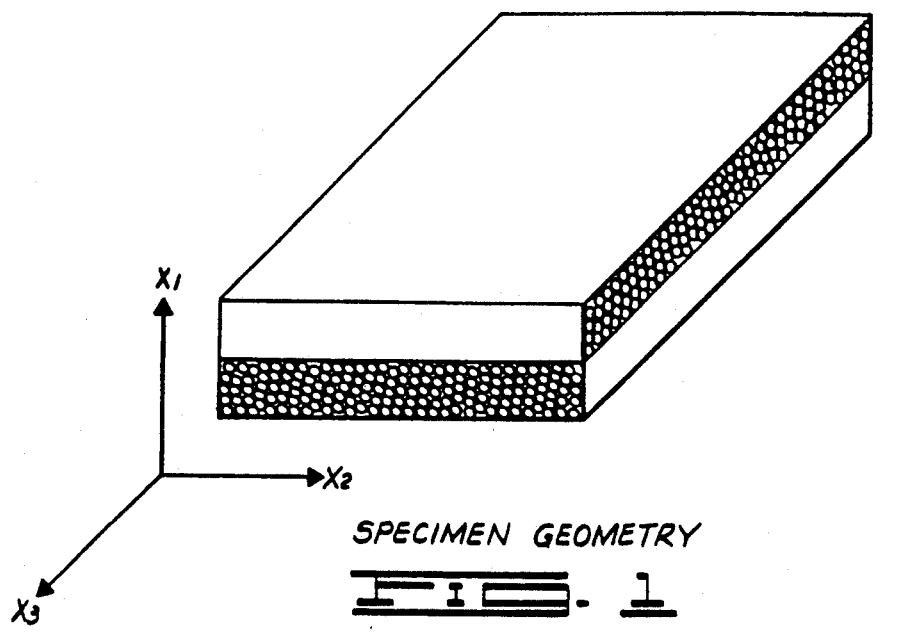
FIG. 1 is a diagrammatic view illustrating the geometry of a specimen of composite material to be tested.

In recent years the use of composite materials has increased significantly. In such materials, two different constituent materials are combined to optimize the properties of the resulting composite material. For example, high strength fiber are embedded in plastic materials to achieve a composite material which is light weight and has a high strength or stiffness to weight ratio. As used herein the term "composite materials" means any material constructed of at least two different constituent materials, and the term includes prepreg discussed and defined below.

Inhomogeneities can develop during the processing stage when the laminate (composite material) is cured to its final solid state.

Unwanted gases may be introduced into the composite material from a variety of sources including entrainment during mixing, entrapment of air between plies during layup and evolution of volatiles during the curing reaction. In an attempt to keep porosity at a minimum, a porous bleed ply usually is placed in contact with the laminate (composite material). In the fabrication process, temperature is increased: initially to lower the resin viscosity for better void and resin transport and ultimately to promote the cure reaction. Simultaneously, pressure is applied to force the unwanted gases and excess resin from the composite into the bleed ply, which is discarded after fabrication. During the process, fibers also can shift position, resulting in areas which are relatively resin rich or resin poor. When the process works properly, the result is a void-free microstructure with a uniform distribution of reinforcing fibers. When the process breaks down, weak areas with excess resin or porosity may be created.

The present invention provides a system for nondestructively determining fiber volume fraction, the percent of volume occupied by one of the constituent materials (fibers), and resin porosity, the percent of volume that is void or occupied by air, in composite materials.

In the present system, the following parameters of the composite material to be tested are taken as known: density, elastic moduli of the constituent materials and layup sequence.

Wave Propagation

The equations of motion for a continuum are given by:

$$\rho \ddot{u}_i = \sigma_{ij,j} \quad (1)$$

where
$\rho$ = density
$\underline{u}$ = particle displacement
$\sigma_{ij}$ = stress tensor components
and i signifies differentiation w.r.t. indicated subscript. By inserting the stress-strain relationship for an anisotropic solid:

$$\sigma_{ij} = C_{ijkl} \epsilon_{kl} \quad (2)$$

where
- $C_{ijkl}$ = elasticity tensor components
- $\epsilon_{kl}$ = strain tensor components into the equations of motion, Eq. (1) becomes:

$$\rho \ddot{u}_i = C_{ijkl} u_{k,lj} \quad (3)$$

Assuming a plane wave solution of the form $$u_i = A_\sigma a_i e^{i(kl\underline{x} - wt)} \quad (4)$$

where
- w = frequency
- k = wave number
- l = wave normal
- $A_\sigma$ = amplitude of particle displacements
- $\alpha$ = displacement (direction cosines)

we obtain the following eigenvalue equation for the velocities of ultrasonic wave propagation in any direction ($l_1$, $l_2$, $l_3$) in an anisotropic material $$\rho w^2 a_i = C_{ijkl} k^2 l_j l_l \alpha_k \quad (5)$$

$$0 = (C_{ijkl} l_j l_l - \rho V_{ik}^2) \alpha_k, \quad V = \frac{w}{k}$$

The geometry of the problem is illustrated in FIG. 1, where the plane of fiber reinforcement has been chosen to be the $x_2$-$x_3$ plane. Since most composite applications are for plate type structures, we are limited for most practical cases to wave propagation in the direction perpendicular to the reinforcing plane, i.e., $l = (1,0,0)$. For this case, the eigenvalue equation for an orthotropic material assumes the form:

$$\begin{pmatrix} C_{1111} - \rho V^2 & 0 & 0 \\ 0 & C_{1313} - \rho V^2 & 0 \\ 0 & 0 & C_{1212} - \rho V^2 \end{pmatrix} \begin{pmatrix} \alpha_1 \\ \alpha_2 \\ \alpha_3 \end{pmatrix} = \begin{pmatrix} 0 \\ 0 \\ 0 \end{pmatrix} \quad (6)$$

which yields three possible wave motions: one pure mode longitudinal wave with velocity $\sqrt{C_{1111}/\rho}$ and two pure mode shear waves with velocities $\sqrt{C_{1313}/\rho}$ and $\sqrt{C_{1212}/\rho}$. For wave propagation in any anisotropic material, one must be concerned with possible complications from energy flux deviations from the wave normal. However, for pure mode longitudinal wave propagation, energy can never deviate from the wave normal. Furthermore energy flux deviation is not observed for pure mode shear wave propagation in a direction perpendicular to a plane of reflection symmetry. Therefore, if we restrict our attention to symmetric laminates (this encompasses virtually all practical laminate stacking sequences), energy flux deviation may be safely neglected.

Material Properties

In order to assess the effects of resin porosity and fiber loading on ultrasonic behavior, it is necessary to first consider the behavior of a single ply in the context of micromechanics. Since voids will reside completely in the matrix, we begin by using the expressions of Boucher, "On the Effective Moduli of Isotropic Two-Phase Elastic Composites". *J. Composite Materials*, Vol. 8, 1974, pp. 82-89, to modify the material properties of an ideal matrix to account for the presence of porosity.

The next step in the procedure is to determine the mechanical properties of each individual ply from the known properties of the reinforcing fibers and the calculated properties of the resin. This micromechanics problem has been the subject of extensive research using a variety of different approaches. Unfortunately, there are no exact solutions available for the problem of a random array of cylindrical reinforcing fibers embedded in an isotropic matrix. However, several investigators have developed suitable expressions (bounds) for the elastic moduli of fiber reinforced composites which can be used as approximations for this purpose. In this investigation, the expressions developed by Hashin, "On the Elastic Behavior of Fiber Reinforced Materials of Arbitrary Transverse Phase Geometry," *J. Mech. Phys. Solids*, Vol. 13, 1965, pp. 119-134, for the upper bounds on the pertinent moduli were used, based on their accuracy and ease of implementation on a minicomputer.

Once the ply properties have been determined, it is then necessary to combine the individual properties in an appropriate manner for the particular stacking sequence to obtain the overall laminate properties. This is done using the equations of classical laminate theory.

The procedure for determining porosity and fiber volume fraction is outlined below.

Ultrasonic Velocity Measurement

A variety of analog techniques are available for the precise determination of transit time for ultrasonic wave propagation, Truell, R., Elbaum, C., and Chick, B., *Ultrasonic Methods in Solid State Physics*, Academic Press, 1969. Any of these methods would be acceptable for this purpose. However, the advent of high speed digital data acquisition and processing techniques means that this process can be automated. In this application we employ a technique developed by Egle, D., "Using the Acoustoelastic Effect to Measure Stress in Plates", UCDL-52914, Lawrence Livermore Laboratory (1980) to achieve this end. This process requires initially that the ultrasonic signals be digitized. An autocorrelation algorithim is then employed to estimate the transit time through the material. This estimate is then refined, using a curve fitting technique to find the maximum in the autocorrelation function. This approach has been found to yield the necessary accuracy in transit time measurements (to within 1 nanosecond) for microstructure characterization.

Data Analysis

Figure 2:
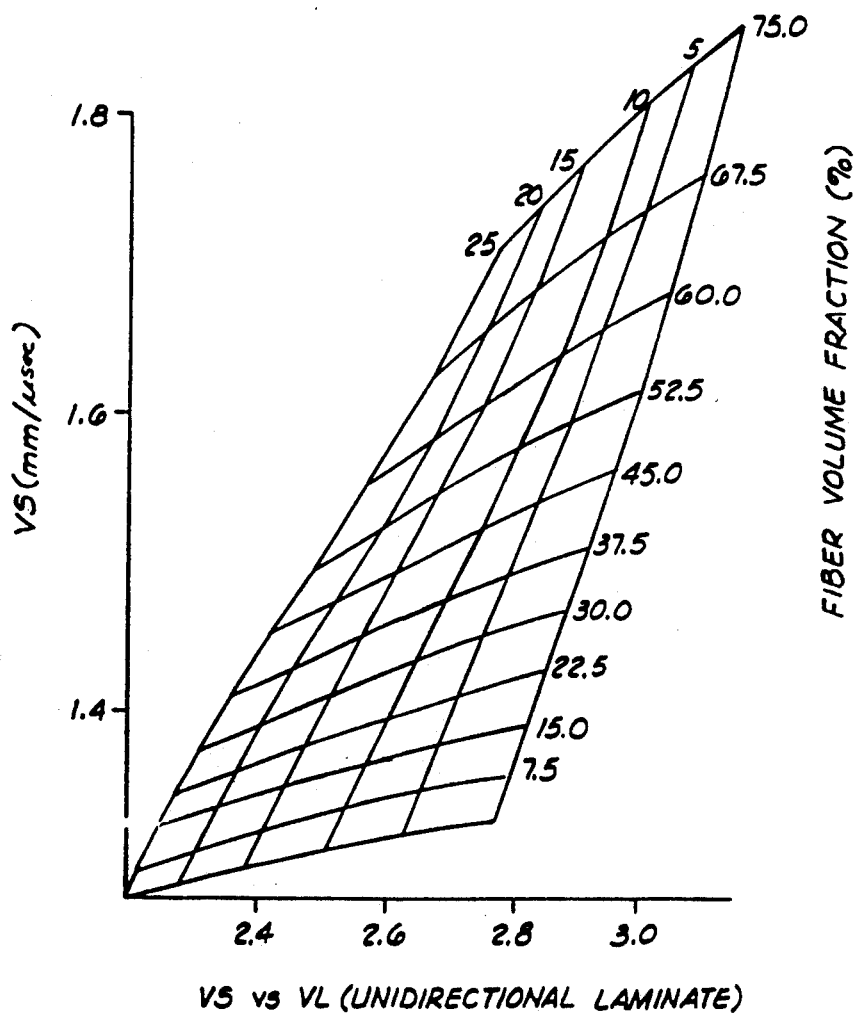
FIG. 2 is a chart illustrating the effects of fiber volume fraction and resin porosity on wave propagation for a typical graphite-epoxy laminate composite material.

The effects of fiber volume fraction and resin porosity on wave propagation for a typical graphite-epoxy laminate configuration are shown in FIG. 2. This figure is based on typical values for the mechanical properties of the constituent materials are shown in Table 1.

TABLE I

| | Mechanical Properties of Composite Constituent Materials | | | |
|---|---|---|---|---|
| | Density (gm/cc) | k (GN/m) | m (GN/m) | G (GN/m) |
| Resin | 1.26 | 7.7 | 2 | 2 |
| Graphite | 1.77 | 14.9 | 5.5 | 24 |

The layups studied in this program include a unidirectional laminate (shown) two cross-ply laminates, two angle ply laminates, and a quasi-isotropic laminate. It should be noted that the velocity approach to fiber fraction/porosity measurement is also applicable to other composite systems (fiberglass, Kevlar, metal-matrix, etc.). However, resolution capability may vary from system to system, depending upon the relative differences in material properties between the fiber and matrix.

The algebraic complexity of the problem (see theoretical section) makes it relatively difficult to solve explicitly for even the simple case of unidirectional reinforcement. For practical laminates, the situation is even more complicated. Clearly, an alternative approach is needed. Ideally, this approach should be rapid, accurate, sufficiently flexible to handle various composite systems and configurations, reliable and easy implement on a commonly available device such as a personal computer. A computer code with these desired characteristics was developed.

Figure 3A:
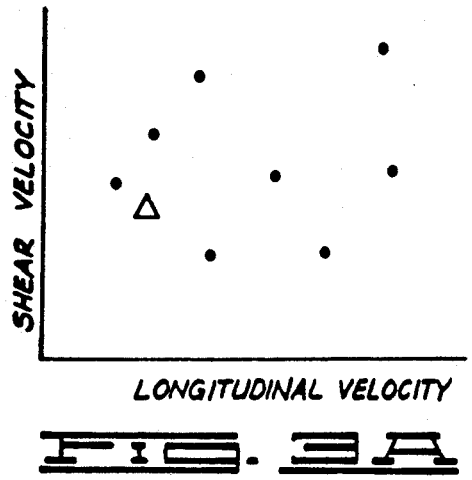
FIG. 3A, 3B and 3C are a series of three diagrams illustrating an iterative search algorithm for determining fiber volume fraction and resin porosity.
Figure 3B:
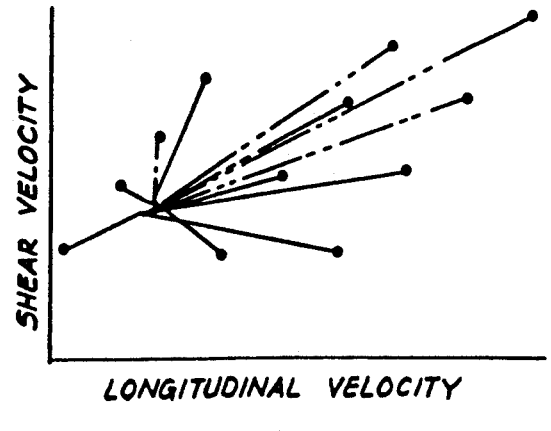
Figure 3C:
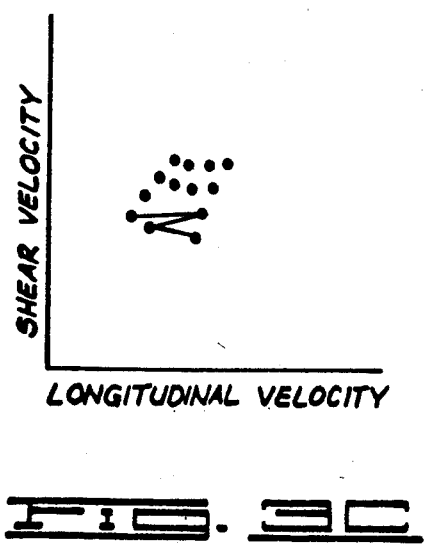

An iterative search algorithim was devised. It is illustrated in FIG. 3. First the points corresponding to the measured velocities are located for varying fiber volume fractions from 25% to 75% in 5% increments for the coarse mesh and resin porosities 0% to 25% in 5% increments. The distance in velocity space is given by:

$$\text{Distance} = [(VL_{Measured} - VL_{Calculated})^2 + (VS_{Measured} - VS_{Calculated})^2]^{\frac{1}{2}}$$

between each of the mesh points of the coarse mesh and the point corresponding to the measured velocities. The mesh point closest to the measured point is then the one which minimizes the distance measure as defined above. Once this point is identified, it serves as the base point for a new mesh with finer increments (+1% in both porosity and fiber content) than that of the original coarse mesh. The process is then repeated to identify the nearest point among the elements of the second mesh to that measured. Then, the entire process is repeated one last time with a relatively fine mesh (+0.1% increments) to establish the final solution. While further refinements are possible by repeating the process indefinitely, differences on this order have little physical significance and do not justify the additional time which would be required to further refine the calculation. The ability of the technique to resolve fine microstructural differences is also limited by the time resolution capability of the pulse-echo overlap technique. In this case, we were capable of measuring transit time differences of 1 nanosecond.

Experimental Verification

In order to assess the utility of this technique, ultrasonic test results were compared with microscopic measurements of porosity and fiber volume fraction. Test samples were machined from a 24 ply, 30.5 cm×30.5 cm unidirectionally reinforced panel manufactured by Lear Fan. This material was fabricated from Fiberite hy-E 1048 prepreg tape using standard autoclave processing techniques.

Figure 4:
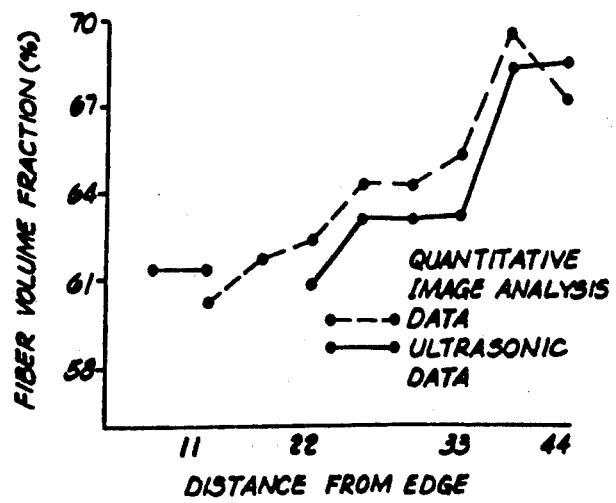
FIG. 4 is a comparison of ultrasonic and quantitive image analysis data.

Quantitative measurements of local fiber content and porosity and fiber volume fraction were made along the edges of selected samples using the ultrasonic technique described previously. These measured samples were sectioned and mounted in epoxy for microscopic analysis. Specimens were abrasively polished and placed in a microscope with quantitative image analysis capability (Quantamet) for automated measurement of microstructural constituents. Results from a typical sample are presented in FIG. 4. Good agreement, both qualitatively and quantitatively, was observed between the ultrasonic predictions of local fiber content and the microscopic measurements. Estimates of fiber loading from the two techniques were usually within 3% of each other. Both techniques predicted that there was negligible porosity present in the samples (less than 1.5%). Since there is an inherent uncertainty of 2% in the quantitative image analysis system, better agreement between the two methods was not expected. It should also be pointed out that the two techniques are not measuring precisely the same quantity. The ultrasonic test is sensitive to material property variations in a cylindrical volume (whose diameter is that of the transducer of 0.31 cm in this case). The image analysis approach measures changes averaged over a plane area (0.49 xm×0.34 cm) rather than a volume. Given the level of material inhomogeneity observed in the velocity scans, some differences in the measurement techniques are to be expected.

Accordingly, it may be concluded that the results from the two methods are in substantive agreement, at least within experimental error.

Conclusions

1. A novel method for measuring local fiber content and porosity in composite materials has been developed.
2. The method is based upon a composite micromechanics model for the effects of fiber content and resin porosity on mechanical properties. The computer code developed in this research effort requires only ultrasonic velocity measurements for the microstructure determination.
3. The method is rapid, nondestructive, and applicable to virtually any composite material system with any stacking sequence.
4. Tests have been conducted on samples of a unidirectionally reinforced, 24 ply graphite-epoxy laminate to examine the utility of this method. Comparison of the predictions of local fiber content and porosity from the ultrasonic data and quantitative image analysis indicated that the two techniques were in substantial agreement with one another with the differences observed attributable to experimental error.

EMBODIMENT OF FIG. 5

Figure 5:
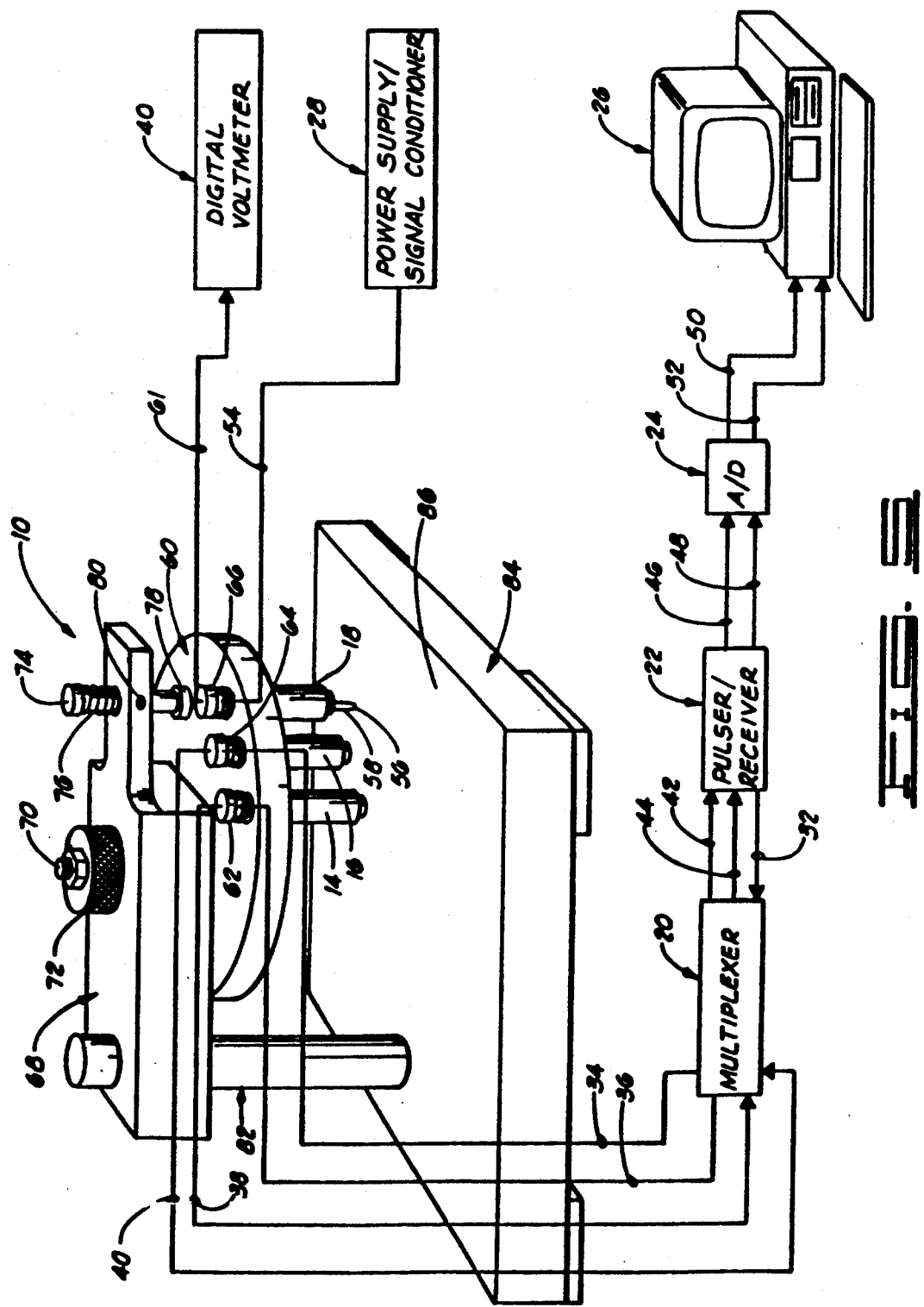
FIG. 5 is a diagrammatic, schematic view of a system constructed in accordance with the present invention for nondestructively determining fiber volume fraction and resin porosity of composite materials.

Shown in FIG. 5 is a system 10 which is constructed to nondestructively determine fiber volume fraction and resin porosity of a composite material in accordance with the present invention and in accordance with the technique described in detail before. The system 10 basically includes: a support structure 12 for operatively supporting a shear transducer 14, a longitudinal transducer 16 and a linearly variable displacement transducer 18; a multiplexer 20; a pulser-receiver 22; an analog to digital converter 24 (designated A/D in FIG. 5); a processer 26; a power supply and signal conditioner 28; and a digital voltmeter 30. In one operational embodiment, the system 10 was constructed utilizing the following commercially available components:

| | |
|---|---|
| a. shear transducer 14 | Panametrics, Model V-155 |
| b. longitudinal transducer 16 | Panametrics, Model V-109 |
| c. linearly variable displacement transducer 18 | Shaevitz, Model PCA-220-005 |
| d. multiplexer 20 | Sonotek, Inc., |

|   |   |
|---|---|
| e. pulser-transducer 22 | Model 23HV Panametrics, Model 5052 |
| f. analog to digital converter 24 | Sonotek, Inc., Model STR *825 an associated software |
| g. processor 26 | Zenith, Model 248 |
| h. power supply and signal conditioner 28 | Albia Electronics Model DM-6 |
| i. digital voltmeter 30 | Hewlett Packard Model 3440 |

In the operational embodiment just described, the particular analog to digital converter 24, Sonotek, Inc. STR *825, plugs directly into the processor 26 and the software associated with this particular analog to digital converter 24 is operatively disposed in the processor 26 for operating the analog to digital converter 24.

The pulser receiver 22 is constructed and adapted to output timed excitation pulses over a signal path 32 to either the longitudinal transducer 16 or shear transducer 14. The pulser receiver also serves to amplify the sensed acoustic waves by the two transducers. The multiplexer 20 allows the operator to automatically switch between the longitudinal transducer 16 or shear transducer 14 as needed.

The excitation pulses are received by the shear transducer 14 or longitudinal transducer 16 and the transducers are constructed to cause an ultrasonic wave to propagate in the test sample, in response to receiving such excitation pulses.

The shear transducer 14 and the longitudinal transducer 16 each also are constructed to receive ultrasonic or acoustic waves propagated through the composite material being tested and to output in an analog format such received waves. The shear transducer 14 outputs received waves propagated through the composite material to be tested over a signal path 38. The longitudinal transducer 18 outputs in an analog format received waves propagated through the composite material to be tested over a signal path 40.

The waves propagated through the composite material are sensed by transducers and outputted by the shear transducer 14 and the longitudinal transducer 16 over the respective signal paths 38 and 40. These analog signals are inputted into and received by the multiplexer 20. The multiplexer 20 outputs the waves propagated through the composite material and received from the shear transducer 14 over a signal path 42 which are inputted into the pulser receiver 22. The multiplexer 20 also outputs the waves propagated through the composite material and received from the longitudinal transducer 16 over a signal path 44 which are inputted into the pulser receiver 22. The pulser receiver 22 outputs the waves propagated through the composite material in an analog format received from the shear transducer 14 over a signal path 46 which is inputted into the analog to digital converter 24. The pulser receiver 22 also outputs the waves propagated through the composite material in an analog format over a common signal path 48 which is inputted into the analog to digital converter 24.

The analog to digital converter 24 digitizes the received waves outputted by the shear transducer 14 and the analog to digital converter 24 outputs the digitized waves over a signal path 50. The analog to digital converter digitizes the waves outputted by the longitudinal transducer 16 and outputs the waves in a digital format over a signal path 52. The digitized waves outputted by the shear transducer 14 and the longitudinal transducer 16 respectively are inputted into the processor 26 by way of the respective signal paths 50 and 52.

The linearly variable displacement transducer 18 is connected to and receives power from the power supply and signal conditioner 28 over a signal path 54. The linearly variable displacement transducer 18 has a contact end 56 on a plunger 58 which is spring loaded and mounted within the casing of the linearly variable displacement transducer 18. The linearly variable displacement transducer 18 is constructed to output a dc voltage proportional to the displacement of the plunger 58 over a signal path 61 which is inputted into the digital voltmeter 40. The digital voltmeter 40 is constructed and adapted to provide a visually perceivable output indication of the voltage of the signal on the signal path 61 which is proportional to the displacement of the plunger 58 in the linearly variable displacement transducer 18 or, in other words, which is proportional to the thickness of the composite material as will be made more apparent below.

The shear transducer 14, the longitudinal transducer 16 and the linearly variable displacement transducer 18 are operatively mounted on the support structure 12. More particular, the shear transducer 14 is disposed through an opening in a cylindrically shaped support plate 61 and the upper end of the shear transducer 14 is supported a distance above the upper surface of the support plate 60 by way of a spring 62 which is disposed about the shear transducer 14 and biases the shear transducer 14 in an upward direction. The longitudinal transducer 16 is disposed through an opening in the support plate 60 and the upper end of the longitudinal transducer 16 is support distance above the surface of the support plate 60 by way of a spring 64 which biases the longitudinal transducer 16 in an upwardly direction. The linearly variable displacement transducer 18 is disposed through an opening in the support plate 60 and the upper end of the linearly variable displacement transducer is supported a distance above the upper surface of the support plate 60 by way of a spring 66 which is disposed about the linearly variable displacement transducer 18.

The support plate 60 is disposed generally below an arm 68. A shaft 70 is disposed through a portion of the arm 68. One end of the shaft 70 is secured to a central portion of the support plate 60. The opposite end of the shaft 70 extends through a knob 72 and the shaft 70 is secured to the knob 72. The shaft 70 is connected to the support plate 60 and the knob 72 so that, by manually rotating the knob 72, the support plate 60 is rotated.

An actuator post 74 is disposed through an opening in one end of the arm 68 and the actuator post 74 is supported within this opening by way of a spring 76 so that one end of the actuator post 74 is supported a distance above the upper surface of the arm 68 by way of the spring 76. The actuator post 74 is supported on the arm 68 so that an actuating end 78 of the actuator post 74 is supported and disposed a distance above the upper surface of the support plate 60 in a nonactuated position of the actuator post 74. A set screw 80 is disposed through a portion of the arm 68 and one end of the set screw 80 is positioned to contact a portion of the actuator post 74 in one position of the set screw 80 to secure the actuator post 74 or the transducers 14 or 16 in a predetermined position within the respective openings in the arm 68 during the operation of the system 10 in a manner and for reasons which will be made more apparent below.

One end of the arm 68 is secured to one end of a support rod 82 and the opposite end of the support rod 82 is secured to a base 84. The support rod 82 cooperates to support the arm 68 and the support plate 60 a distance above an upper surface 86 of the base 84. The support rod 82 also is sized so that the shear transducer 14, the longitudinal transducer 16 and the linearly variable displacement transducer 18 each are supported a predetermined distance above the upper surface 86 of the base 84.

In operation, the composite material to be tested is placed on the upper surface 86 of the base 84 in a position generally under the plunger 58 contact end 56 of the linearly variable displacement transducer 18. The actuator post 74 is then pressed manually against the bias action of the spring 76 thereby moving the actuating end 78 into engagement with the upper end of the linearly variable displacement transducer 18. The actuator pulse 70 is manually moved in the downward direction until the upper end of the linearly variable displacement transducer 18 engages the upper surface of the support plate 60. The actuator post 74 can be secured in this position by the set screw 80 if desired. In this position of the linearly variable displacement transducer 18, the DC voltage outputted by the linearly variable displacement transducer 18 over the signal path 61 is proportional to the thickness of the composite material being tested and this voltage proportional to thickness is outputted over the signal path 61 and inputted into the digital voltmeter 40. The digital voltmeter 40 provides a visually perceivable output indication indicating the DC volt of the signal inputted on the signal path 61, this voltage being proportional to the thickness of the composite material. The operator manually inputs the thickness of the composite material into the processor 26 using the processor 26 keyboard.

It should be noted that, in a more automated form or if desired in a particularly application, the linearly variable displacement transducer 18 output signal proportional to the thickness of the material can be inputted directly into the processor 26 thereby eliminating the manually steps of reading the digital voltmeter 40 in manually inputting the thickness into the processor 26 if desired.

The actuator post 74 then is released and moved by the spring 76 to the rest position shown in FIG. 5 thereby causing the linearly variable displacement transducer 18 to be moved to the rest position by the spring 66. After the linearly variable displacement transducer 18 has been moved to the rest position, the operator then rotates the knob 72 thereby rotating the support plate 60 to position the upper end of the longitudinal transducer 16 generally under the actuating end 78 of the actuator post 74. The actuator post 74 then is moved downwardly against the bias action of the spring 76 with the actuating end 78 thereof engaging and moving the longitudinal transducer 16 in the downwardly direction. The longitudinal transducer 16 is moved in the downwardly direction by the actuator post 74 until the lower end of the longitudinal transducer 16 engages the upper surface of the composite material. The actuator post 74 is secured in this position by the set screw 80 thereby securing the longitudinal transducer 16 in the operating position wherein the lower end of the longitudinal transducer 16 engages the upper surface of the composite material.

It should be noted that, prior to moving the longitudinal transducer 16 to the operating position just described, a high viscosity coupling agent is applied to the lower end of the longitudinal transducer 16 for coupling the ultrasonic vibrations of the longitudinal transducer 16 to the composite material to be tested. Also, the high viscosity coupling agent is applied to a portion of the upper surface of the composite material to be tested. One coupling agent suitable for this purpose is a resin made by Dow Chemical, Model V9.

After the longitudinal transducer 16 has been moved to the operating position, the pulser receiver 22 is actuated to output exitation pulses which are multiplexed through the multiplexer 20 and inputted into the longitudinal transducer 16 by way of the signal path 34. The longitudinal transducer 16 is constructed to vibrate in a particular manner so that longitudinal ultrasonic waves are couple to and propagated through the composite material. The ultrasonic waves induced by the longitudinal transducer 16 and propagated through the composite material to be tested propagate through the composite material and are reflected back through the composite material (back surface reflections in the particular embodiment of the invention shown in FIG. 5). The ultrasonic waves propagated through the composite material and reflected back through the composite material are sensed and received by the longitudinal transducer 16, and the longitudinal transducer 16 outputs an analog signal on the signal path 40 in response to receiving the ultrasonic waves propagated through the composite material. These received signals are outputted on the signal path 40 in an analog format. The signals outputted by the longitudinal transducer 16 on the signal path 40 are indicative of a second velocity ($V_2$), the velocity of the ultrasonic wave propagated through the composite material emanating from the longitudinal transducer 16.

The transducers 14, 16 and 18 must be positioned in the same position during the operation of the system 10 so the thickness measurement is taken and the ultrasonic waves are propagated through substantially the same point on the composite material. Index marks could be inscribed on the upper surface of the support plate 60 for alignment with one edge of the arm 68 to visually align each of the transducers 14, 16 and 18. In the alternative, index holes can be formed in the upper surface of the support plate 60 and a ball can be located in an opening in the lower surface of the arm 68 with the ball being biased toward the arm 68 by way of a spring. Thus, when the support plate 60 is rotated, the ball falls into one of the index holes in the support plate 60 to indicate that the support plate 60 has been rotated to a correct position.

The signals outputted by the longitudinal transducer 16 are multiplexed through the multiplexer 20 and inputted into the pulser receiver 22 by way of the signal path 44. The pulser receiver outputs such signals on a signal path 46 for reception by the analog to digital converter 24. The analog to digital converter 24 receives the signals in the analog format outputted by the longitudinal transducer 16 and the analog to digital converter 24, operated by the processor 26 in accordance with the program mentioned before for operating the analog to digital converter 24, digitizes the analog signals outputted by the longitudinal transducer 16. The analog digital converter 24 outputs in a digital format the longitudinal transducer 16 output signals on the signal path 52 which are inputted into the processor 26. The processor 26 is programmed to determined the second velocity ($V_2$) in response to receiving the inputted transducer 16 output signals in the digital format from the analog to digital converter 24.

The actuator post 74 then is released and moved by the spring 76 to the rest position shown in FIG. 5 thereby causing the longitudinal transducer 16 to be moved to the rest position by the spring 64. After the longitudinal transducer 16 has been moved to the rest position, the operator then rotates the knob 72 thereby rotating the support plate 60 to position the upper end of the shear transducer 14 generally under the actuating end 78 of the actuator post 74. The actuator post 74 then is moved downwardly against the bias action of the spring 76 with the actuating end 78 thereof engaging and moving the shear transducer 14 in the downwardly direction. The shear transducer 14 is moved in the downwardly direction by the actuator post 74 until the lower end of the shear transducer 14 engages the upper surface of the composite material. The actuator post 74 is secured in this position by the set screw 80 thereby securing the shear transducer 14 in the operating position wherein the lower end of the shear transducer 14 engages the upper surface of the composite material.

It should be noted that, prior to moving the shear transducer 14 to the operating position just described, a high viscosity coupling agent is applied to the lower end of the shear transducer 14 for coupling the ultrasonic vibrations of the shear transducer 14 to the composite material. One coupling agent suitable for this purpose is a resin made by Dow Chemical, Model V9, as mentioned before.

After the shear transducer 14 has been moved to the operating position, the pulser receiver 22 is actuated to output excitation pulses which are multiplexed through the multiplexer 20 and inputted into the shear transducer 14 by way of the signal path 34. The shear transducer 14 is constructed to vibrate in a particular manner so that shear ultrasonic waves of a known polarization are coupled to and propagated through the composite material. The ultrasonic waves induced by the shear transducer 14 and propagated through the composite material to be tested propagate through the composite material and are reflected back through the composite material (back surface reflection in the particular embodiment of the invention shown in FIG. 5). The ultrasonic waves propagated through the composite material and reflected back through the composite material are sensed and received by the shear transducer 14. The shear transducer 14 outputs an analog signal on the signal path 40 in response to receiving the ultrasonic waves propagated through the composite material, these received signals being outputted on the signal path 40 in an analog format. The signals outputted by the shear transducer 14 on the signal path 40 are indicative of the velocities of the two ultrasonic waves (($V_1$ and $V_2$) propagated through the composite material by the shear transducer 14.

The signals outputted by the shear transducer 14 are multiplexed through the multiplexer 20 and inputted into the pulser receiver 22 by way of the signal path 44. The pulser receiver outputs such signals on a signal path 46 for reception by the analog to digital converter 24. The analog to digital converter receives the signals in the analog format outputted by the shear transducer 14 and the analog to digital converter 24, operated by the processor 26 in accordance with the program mentioned before for operating the analog to digital converter 24, digitizes the analog signals outputted by the shear transducer 14. The analog to digital converter 24 outputs in a digital format the shear transducer 14 output signals on a signal path 52 which are inputted into the processor 26. The processor 26 is programmed to determined the first velocity ($V_1$) (the velocity of the factor of the two shear waves) in response to receiving the inputted transducer 16 output signals in a digital format from the analog to digital converter 24.

Prior to starting the operation of the system 10, the operator manually has inputted into the processor 26 certain parameters of the composite material to be tested, namely, density, elastic moduli of the constituent materials and layup sequence, which are stored in the processor 26. The processor 26 previously has the thickness of the composite material also has been inputted into the processor 26 in the manner described before.

The processor 26 is programmed to store the inputted thickness of the composite material to be tested. After the processor 26 has determined the first and second velocities, $V_1$ and $V_2$, the processor 26 then is programmed to determined the fiber volume fraction and resin porosity of the composite material based on the determined parameters of thickness and first and second velocities, $V_1$ and $V_2$, and the inputted known parameters of density, elastic moduli of the constituent materials and layup sequence in accordance with the procedures graphically shown in FIGS. 2 and 3 and described before. In one particular embodiment, the processor 26 was programmed with the following program to enable the processor 26 to determine the fiber volume fraction and resin porosity of the composite material to be tested in the manner just described, the program being outlined below in the FORTRAN and C (subroutine PLT_Time) languages:

```
c      ------------------------------------------------
c      This program will compute the fiber volume
c      fraction and porosity of a laminated composite
c      (composed of layers of a uni-directional
c      composite material), based on the measured
c      longitudinal and shear velocities.
c      ------------------------------------------------
       interface to function pltime[c,alias:'_plot_
       time'] (n)
       integer n
       end
       interface to subroutine stinit[c]
       end
c
```

```
      dimension v1(11,11),vs(11,11),vl(11,11),v2(11,
11) space(3)
      dimension a(10,2)
      real c(2),t
      real mpsm, msm
      integer m1,m2,m3
      character infile*12
      common fsum,fden,rden,mpsm,msm,fpsm,ftsm,
flsm,nang
c
      data a,v1,vs,vl,v2/504*0.0/
      call stinit
      fsum = 0.0
c
c      ------INPUT MATERIAL PROPERTIES FOR----------
c      -----------FIBER-MATRIX SYSTEM--------------
c
5     print*, ' ENTER THE NAME OF THE INPUT DATA
FILE'
      read(*,103) infile
103   format(a)
      open(3,file=infile,status='old')
      read(3,*) fden
      read(3,*) rden
      read(3,*) mpsm
      read(3,*) msm
      read(3,*) fpsm
      read(3,*) ftsm
      read(3,*) flsm
      rewind(unit=3)
      print*, ' ENTER THICKNESS OF THE SPECIMEN'
      read*, thick
      print*, ' ENTER NUMBER OF DIFFERENT ORIENTATION
ANGLES IN',
     &         ' LAYUP'
      read*, nang
      do 10 i=1,nang
      print*, ' ENTER ORIENTATION ANGLE IN RADIANS'
      read*, a(i,1)
      print*, ' ENTER NUMBER OF PLIES AT THIS ANGLE'
      read*, a(i,2)
      fsum = fsum + a(i,2)
10    continue
c
c-------CALCULATE WAVE VELOCITY DATA---------
c
15    do 20 i = 2,1,-1
      t=pltime(n)
      c(i) = thick/(t*1000.)
20    continue
c
c------------------SET AND REFINE MESH--------------
c
      space(1)=0.05
      space(2)=0.01
      space(3)=0.001
      ff=0.25
```

```
      fv=0.0
      do 25 k = 1,3
      call mesh(a,space(k),ff,fv,vl,vs,v1,v2)
      fmin = 1.e05
      do 30 i = 1,11
      do 40 j = 1,11
      fd = sqrt((vl(i,j) - c(1))**2 + (vs(i,j) -
c(2))/(2)
      if( fd .lt. fmin ) then
      fmin = fd
      imin = i
      jmin = j
      endif
40    continue
30    continue
c
c------------SET LOWER LIMITS FOR NEW MESH----------
c
      if( k .lt. 3 ) then
      ff = v1(imin,jmin) - 5.*space(k+1)
      fv = v2(imin,jmin) - 5.*space(k+1)
      if(( fv .lt. 0.0 ) fv = 0.0
      endif
25    continue
      ff = v1(imin,jmin)*100.
      fv = v2(imin,jmin)*100.
      write(*,105) c(1)*1000.
      write(*,106) c(2)*1000.
105   format(1x,'THE LONGITUDINAL WAVE SPEED
IS:',1x,f7.1,1x,'m/s')
106   format(1x,'THE SHEAR WAVE SPEED
IS:',1x,f7.1,1x.'m/s')
      write(*,100) ff
      write(*,101) fv
100   format(1x,'THE FIBER VOLUME FRACTION
IS:',1X,f6.2 .' %')
101   FORMAT(1x,'THE RESIN VOID CONTENT IS:'1x,f6.2,'
%,/)
      write(*,102)
102   format(1x,'&0-STOP, 1-CONTINUE TESTING SAMPLE,
 2-CHANGE MATERIAL'
     & ,1x,'CONSTANTS')
      read(*,*) m1
      if(m1 .eq. 1) go to 15
      if(m1 .eq. 2) go to 5
      stop
      end
c
      subroutine mesh(a,s,ff,fv,vl,vs,v1,v2)
      dimension a(10,2),vl(11,11),vs(11,11),
v1(11,11),v2(11,11)
      do 10 i=1,11
      vf = fv
      do 20 j=1,11
      call coef(a,ff,vf,ft1,ft2)
      vl(i,j)=ft1
      vs(i,j)=ft2
```

```
      v1(i,j)=ff
      v2(i,j)=vf
      vf=vf+s
20    continue
      ff=ff+s
      continue
      return
      end
c
      subroutine coef(a,ff,vf,ft1,ft2)
      dimension a(10,2)
      real mpsm,msm
      common fsum,fden,rden,mpsm,msm,fpsm,ftsmflsm,
     ,nang
      fve = vf
c     fve = vf/(1. - ff)
      ft = 1. - fve
      fdm = ft*rden
      fgs = msm*(9.*mpsm + 8.*msm)/(6.*(mpsm +
     2.*msm))
      fkm = mpsm*(1. - fve/(1. - ft*mpsm/(1.3333*msm
     + mpsm));
      fmm = msm*(1. - fve/(1. - ft*msm/(msm + fgs)))
      fdc = fdm + ff*(fden - fdm)
      fmc = (fkm + 2.*fmm)*(1. - ff)/(2.*fmm*(fkm +
     fmm))
      fmc = ff/(1./(ftsm - fmm) + fmc) + fmm
      fkc = fkm + ff/(1./(fpsm - fkm) + (1. -
     ff)/(fkm + fmm)) + fmc
      fgc = fmm + ff/(1./(flsm - fmm) + 1. -
     ff)/(2.1fmm)
      c44 = 0.0
      c66 = 0.0
      c46 = 0.0
      do 10 j = 1,nang
      ct = a(j,2)/fsum
      c44 = ct*(fmc*sin(a(j,1))**2 +
     fgc*cos(a(j,1)))** 2) + c44
      c66 = ct*(fmc*cos(a(j,1))**2 +
     fgc*sin(a(j,1))** 2) + c66sin(a(j,1))*
      c46 = ct*(cos(a(j,1))*sin(a(j,1))*(fgc - fmc))
     + c46
10    continue
      x = sqrt((c44+c66)**2 - 4.*(c44*c66 - c46**2))
      x1 = (c44 + c66 - x)/2.
      x2 = (c44 + c66 -x)/2.
      ft1 = sqrt(fkc/fdc)
      ft2 = sqrt(max(x1,x2)/fdc)
      return
      end include <stdlib.h>
include <stdio.h>
#include <str_plx.h>
#include <str_str.h>
#include <graph.h>
```

```c
        struct plot sp[1]={1,1,608,15, 136,
73,198,2,0,1,2,1};

extern struct str sa[1];
        char buff[4096]={0};

int ipm = 2;
        int i,on[2]={1,0};
        unsigned int ick;
        int brd=0;
        int nbs=1;
        int ichar;
        int step=1;
        int     iret=0x0d,exc=0x1b,mov1=0x4b00,movr=
0x4d00,iend=0x1f00,movup=0x4800;
        int     pageup=0x4900,movdn=0x5000,pagedn=0x
5100,del=0x5300,ins=0x5200;
        int     start=70,mid=120,stop=160;

float plot_time(q)
        int q;
        {
        int width,mark[3];
        int ii,rmax,ro;
        int co[1024];
        int kmax,max;
        int j;
        float time;
        float f;

mode(14);
        vigen(11);
        attrib(&sp[0]);
        grid(15,32,19,72,16,10,1,6);
        chrplt("Adjust Pulser-Receiver For Best
Waveform",170,18,15);
        chrplt("Hit ESC To Continue",240,38,18);
            /*data collection and plotting loop*/ sa[0].isr=7;
        i=sa[0].pdel[0]=0;
        sa[0].navg=6;
        j=1;
        chrplt("^",start,127,3);
        chrplt("^",mid,127,4);
        chrplt("^",stop,127,5);
        chrplt("Scanning Window Width =",220,0,7);
        coor(start,220,3);
        coord(mid,320,4);
        coord(stop,420,5);
        while(1){
                strbuf(&sa[0],buff);
                fplot(&ipm,&sp[0],buff;
                ipm=1;
        if(kbhit() != 0){
                ichar = getkey();
```

```
            if(ichar == exc)
            break;
            )
        else if(ichar == 's' || ichar == 'S'){
            coord(start+i,220,3);
            coord(mid+i,320,4);
            coord(stop+i,420,5);
            for(;;){
            ichar=getkey();
            if(ichar == exc)break;
            else if(ichar == del){
                for);;){
                    ichar=getkey();
                    coord(start+i,220,3);
                    if(ichar == movl &&
start > 50+step){
                    chrplt("^",start,
127,3;  );
                    chrplt("^",start-=step,
127,3);
                    )
                else if(ichar == movr && start
<mid-step){
chrplt("^",start,127,3);
                    chrplt("^",start+=step,
127,3);
                    )
                else if( ichar == movup)step
+=2;
                else if( ichar == movdn){
                    step -= 2;
                    if(step <= 1) step=1;
                    )
                    else if( ichar == iret
|| ichar == exc){
                    break;
                    break;
                    )
                    else continue;
                }
            )
        else if(ichar == iend){
            for(;;){
                ichar=getkey();
                coord(mid+i,320,4);
                if(ichar == movl && mid
> start+step){
                    chrplt("^",mid,
127,4);
                    chrplt("^",mid-
=step, 127,1);
                )
                else if(ichar == movr
&& mid < step-step){
                    chrplt("^"mid,
127,1);
                    chrplt("^",mid+
=step,127,4);
                    )
```

```c
            )step+=2;
        )( step=1;

|| ichar == exc){

)
            }
        else if(ichar == pagedn) {
            for(;;){

+step){

);

127,1);

< 591-step){

);

,127,5);

2;

r == exc){

)
          )
         else if( ichar == exc ) break;
          }
      }
    }
    mark[0] = (start+i)*8;
    mark[1] = (mid+i)*8;
    width = mark[1] - mark[0];
    ipm=0;
    fplot(&ipm,&sp[0],buff);
    _setvideomode(_DEFAULTMODE);
    sa[0].isr = 10;
    sa[0].pdel[0]=0;
```

```c
        else if( ichar == movup
        else if( ichar =  movdn step -= 2;
                if(step <= 1)

}
        else if( ichar == iret break;
                break;
            } ichar=getkey();
                coord(stop+i,420,5);
                if(ichar == movl && stop > mid chrplt("^",stop,127,5 chrplt("^"stop-=step,

}
            else if(ichar == movr && stop chrplt("^",stop,127,5 chrplt("^",stop+=step

{
            else if( ichar == movup)step+= else if( ichar == movdn) {
                    step -= 2;
                    if(step <= 1) step=1;
                }
            else if( ichar == iret || icha break;
                    break;
                }
```

```
        strbufr\(&sa[0],buff);
        for(ii=0; ii <=4096-mark[0]; ii==
                buff[ii] = buff[ii+mark[0]];
        for(ii=4097-mark[0]; ii<= 4096; ii++)
                buff[ii] = 0;
        rmax = 0;
        kmax = 0;
        mark[2] = (stop+i)*8 - mark[0];
        for(ii=mark[2]-width; ii,= (mark[2]); ii++){
                ro=autocor(width,ii);
                co[ii-mark[2]] = ro;
                if(rmax < ro){
                        rmax = ro;
                        max = ii - mark[2];
                        kmax = ii;
                }
        }
        f = ((float)(co[max-1] - co[max+1]))/((float)
(co [max-1]-2*co[max]+co[max+1]));
        time = ((float) kmax) + f;
        time *= 5.e-09;
        return(time);
} char word[6][4]=("","","","","","");
char window[2][5]=("","");

coord(j,k,color)
int j,k,color;
{
        sprintf(word[color-3],"%d",j);
        chrplt(word[color],k,10,color);
        chrplt(word[color-3],k,10,color);
        sprintf(word[color],"%s",word[color-
3]);
        sprintf(window[0],"%d",mid-start);
        chrplt(window[1],420,0,7);
        chrplt(window[0],420,0,7);
        sprintf(window[1],"%s",window[0]);
}
autocor(i,j)
int i,j;
{
int k;
float r=0.0
for(k=0; k<=i; k++){
        r += buff[k]*buff[k+j];
}
return(r);
}

NOTE:  This program calls  several subroutines:
     STINIT - board initialization routine
     STRBUF - collects data from A - D
              converter
```

STRDRV - board driver to acquire data from the digitizer. These routines are commercially available from Sonotek. For displaying waveforms, several routines from the "Fastplot" library (also available from Sonotek) are employed.

The signals outputted by the longitudinal transducer 16 and the shear transducer 14 comprise a first series of pulses generally referred to in the art as the "main bang" followed after a time delay by another series of pulses referred to generally in the art as "first back surface reflections", followed after a time delay by another series of pulses commonly referred to in the art as "second back surface reflections". This sequence of a series of pulses followed by a time delay and then another series of pulses is repeated. The analog to digital converter 24 digitizes this signal. The processor 26 could then be programmed to determine the velocity ($V_1$) or ($V_2$) by determining the time delay between corresponding peaks of the first and the second back surface reflections. However, in accordance with the program described above and in accordance with one mode of operating the present invention, the processor 26 is programmed to determine this time delay and thus determine the first and the second velocities, ($V_1$) and ($V_2$), using a quadratic fit to find the maximum in the autocorrelation function to determine the peak in each of the first and the back surface reflections and the time delay between these two peaks then is utilized to determine the respective velocities, ($V_1$) and ($V_2$).

It also should be noted that the particular analog to digital converter 24 describe before digitizes at a rate of 25 MKz. This rate of digitizing does not provide the accuracy desired in most applications of the system 10. Thus, the program mentioned before in connection with the particular analog to digital converter 24 cooperates the analog to digital converter 24 to artificially induce a higher accuracy by shifting the point in the analog signal to be digitized eight times thereby providing an effective digitizing rate or sample rate of 200 MHz in this particular example.

Rather than using the autocorrelation function system for determining the peaks for the purpose of measuring the velocities, ($V_1$) and ($V_2$), the processor 26 could be programmed to simply measure or determine the time delay between the peaks of the digitized signal. This is not done in the particular embodiment described before because this has been found not to be as accurate as the method previously described because of dispersion and attenuation phenomena. However, if the analog to digital converter 24 could be operated at a higher sampling or digitizing rate, this peak to peak method could be utilized for higher data acquisition.

With the particular model shown in FIG. 5 and particularly with the specific embodiment shown described before, the outputs of the shear transducer 14 and the longitudinal transducer 16 are displayed by the processor 26 so the operator can determine whether or not the received signals are adequate for processing in accordance with the present invention. The operator is observing these signals on the processor 26 display to ascertain whether or not the amplitudes are high enough or, in other words, whether or not this is a detectable signal. The processor 26 in some applications could be programmed to make this determination automatically.

As specifically described before, the system 10 utilizes a shear transducer 14 and a longitudinal transducer 16. In the shear transducer 14, vibrations are generated in response to the received excitation pulses and these vibrations result in the first ultrasonic wave being emitted from the shear transducer 14 and propagated through the composite material to be tested. Assuming "l" equals a vector describing the direction of propagation of the ultrasonic wave normal, and "$\underline{a}$" equals a vector describing the direction of particle vibration in the composite material, then the ultrasonic wave propagated through the composite material as a result of a shear transducer 14 represent a circumstance where "$\underline{l}$" is perpendicular to "$\underline{a}$".

As specifically described before, the system 10 also utilizes a longitudinal transducer 16. In the longitudinal transducer 16, vibrations are generated in response to the received excitation pulses and these vibrations result in the second ultrasonic wave being emitted from the longitudinal shear transducer 16 and propagated through the composite material to be tested in this circumstance,"$\underline{l}$" is parallel to "$\underline{a}$". Assuming "$\underline{l}$" equals a vector describing the direction of propagation of the ultrasonic wave normal, and "$a$" equals a vector.

Thus, the waves propagated through the composite material as induced by the shear transducer 14 and the longitudinal transducer 16 have different polarizations, one instance, being were "$\underline{l}$" is parallel to "$\underline{a}$" in the case of the longitudinal transducer 16 and the other being were "$\underline{l}$" is perpendicular to "$\underline{a}$" in the case of the shear transducer 14. In the present invention, it only is important that two acoustic waves are propagated through the composite material to be tested having different polarizations and the present application is not limited to the particular polarizations described before with respect to the longitudinal and the shear transducers 16 and 14.

It also should be noted that two waves having different polarizations can be caused to be propagated through the composite material to be tested using only a single shear transducer. In this instance, the composite material to be tested in placed in one position under the single shear transducer for inducing the first ultrasonic wave to be propagated through the composite material. The composite material then is moved and repositioned under the shear transducer for propagating the second ultrasonic wave through the composite material. If the composite material is moved in a proper manner to different positions are just described, two waves having different polarizations can be induced in the composite material using the signal shear transducer.

The specific program described before is particularly adapted for composite materials wherein the fiber constituent is disposed in the other material constituent in a two dimensional pattern. The present invention also could be utilized for three dimensional patters; however, the processor 26 program would have to be modified to accommodate such three dimensional patterns. In general, the program would have to be modified in the following manner to accommodate three dimensional patterns for woven reinforcements, or for carbon-carbon materials.

EMBODIMENT OF FIG. 6

Figure 6:
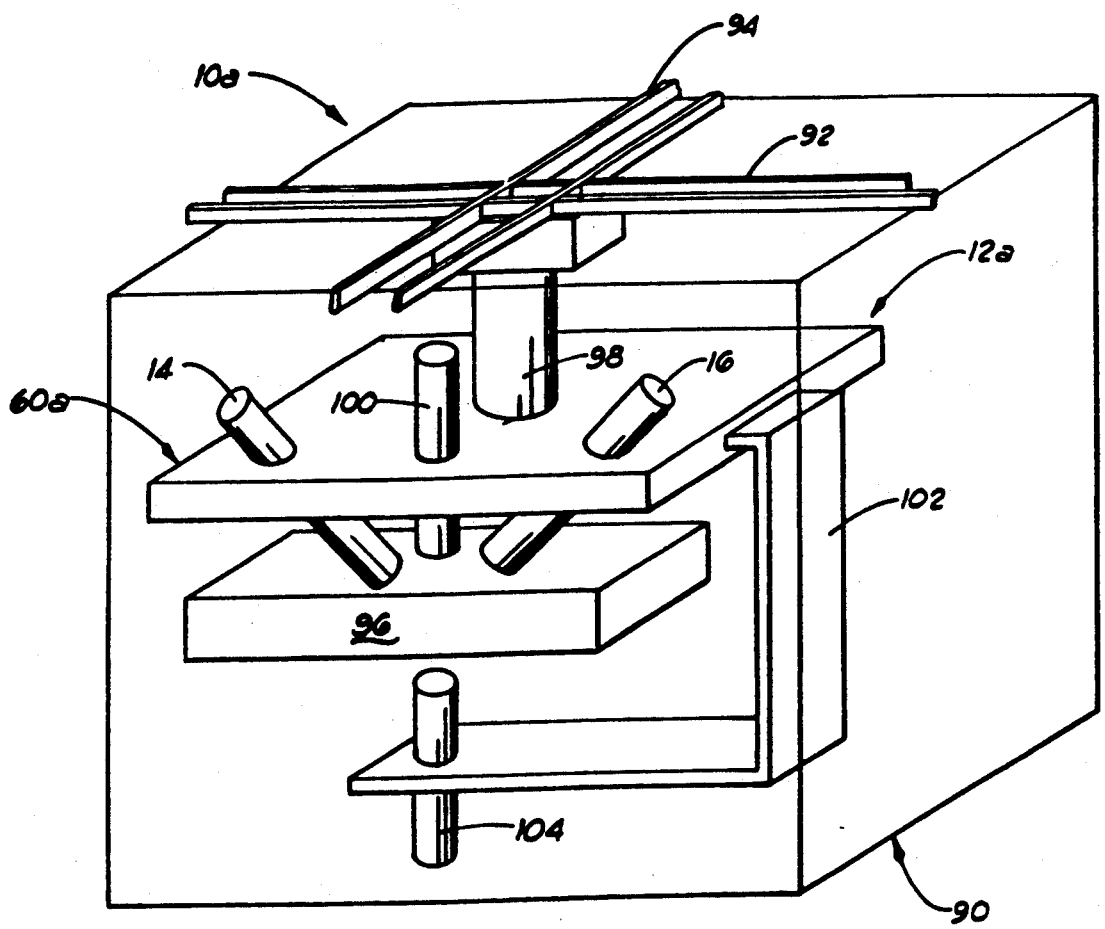
FIG. 6 is another system which is constructed in accordance with the present invention for nondestructively determining fiber volume fraction and resin porosity of composite materials.

Shown in FIG. 6 is a system 10a which also is constructed in accordance with the present invention for nondestructively determining fiber volume fraction and resin porosity of a composite materials. The system 10a generally comprises a modifed support structure 12a which is disposed in a reservoir 90 containing water, the support structure 12a being immersed in the water.

The support structure 12a is connected to cross beams 92 and 94 which are supported on the upper end of the reservoir 90. In this embodiment, the composite material to be tested also is immersed within the reservior as generally illustrated diagrammatically in FIG. 6 wherein the composite material is designated by the reference numeral 96.

The support structure 12a includes a modifed support plate 60a which is rollingly connected to the cross beams 92 and 94 by way of a support beam 98, one end of the support beam 98 being secured to the support plate 60a and the opposite end of the support beam 98 being rollingly connected to the cross beams 92 and 94 so the support plate 60a can be moved along the support beam 92 and alternatively along the support beam 94 for positioning the support plate 92 in various positions within the reservoir 90 and with respect to the composite material 96.

In this embodiment, four longitudinal transducers are used. One pair (100 and 104) are employed at normal incidence for longitudinal wave propagation. A second pair (14 and 16) are employed at an incidence angle other than 90° and are used to generate shear waves via mode conversion. In this way, transducers 100 and 104 can be used for thickness measurement (since they are a known distance apart and the sound velocity in water is constant) as well as for longitudinal wave propagation.

One end of a curved arm 102 is connected to the support plate 60a. The arm 102 extends a distance from the support plate 60a so the opposite end of the arm 102 is positioned generally below and spaced a distance from the first thickness transducer 100. A second thickness transducer 104 is supported in the end of the arm 102, opposite the end connected to the support plate 60a, so that the second thickness transducer 104 is aligned with the first thickness transducer 100. The second thickness transducer 104 also is constructed and operates exactly like the longitudinal transducer 16 described before.

The transducers 14, 16, 100 and 104 each are connected through the multiplexer 20, the pulser receiver 22, the analog to digital converter 24 and the processor 26 in a manner exactly like that described before with respect to the transducers 14 and 16.

In operation, the composite material to be tested is disposed in the immersion bath within the reservoir 90. The support structure 12a is positioned on the cross beam 92 or the cross beam 94 so that transducer 100 is positioned generally above a point on the composite material 96 and transducer 104 is positioned generally on the opposite side of the composite material 96 and aligned with the first thickness transducer 100. In this position, the transducer 14 is angularly disposed within the support plate 60a so that the ultrasonic wave emitted by the transducer 14 impinges on the point immediately below the first thickness transducer 100 and generally between the first and the second thickness transducers 100 and 104. In this position, transducer 16 is angularly disposed within the support plate 60 so that the ultrasonic waves generated in the part by transducer 14 will be received by transducer 16.

Transducer 14 and transducer 16 are operated in a pitch-catch mode rather than the pulse-echo mode described in FIG. 6. Otherwise, they are used to provide shear velocity information analogous to that provided by the single contact shear transducer shown in FIG. 5 (14).

Transducer pair 100 and 104 are used for two purposes. The first purpose is to determine the thickness of the composite sample. For this purpose, transducer 100 is excited by the pulser receiver 22 to generate a longitudinal wave in the water. This wave propagates to the upper surface of the composite material where part of the energy is reflected back to transducer 100. The reflected wave and successive reflections are sensed by this transducer. Since the velocity of sound wave propagation in water is a known constant (1,460 m/s), by digitizing the response of transducer to the first two water path reflections, the distance between transducer 100 can be determined. In a similar fashion, by exciting transducer 104 and digitizing the same two water path echoes, its position relative to the lower surface of the composite is determined. Since the total distance between the surface of transducer 100 and transducer 104 is fixed, this procedure yields the thickness of the composite.

The second purpose of the transducer pair is to determine the velocity of longitudinal wave propagation in a direction perpendicular to the plane of reinforcement. The device may be operated in a pulse-echo mode with a single transducer (either 100 or 104) serving as generator and receiver or with one transducer serving as generator and the other as receiver. By now analyzing successive internal reflections within the composite, the transit time for this digital mode can be measured. This, in conjunction with the thickness measurement, yields the desired longitudinal velocity ($V_2$).

In this operation of system 10a, the first and second velocities are determined in a manner similar to that described with respect to system 10 and the processor is programmed to calculate resin porosity and fiber volume fraction as in system 10. The processor is also programmed to translate the transducer assembly over the surface of the part so that resin porosities and fiber volume fraction measurements can be performed for the entire part.

EMBODIMENT OF FIG. 7

Figure 7:
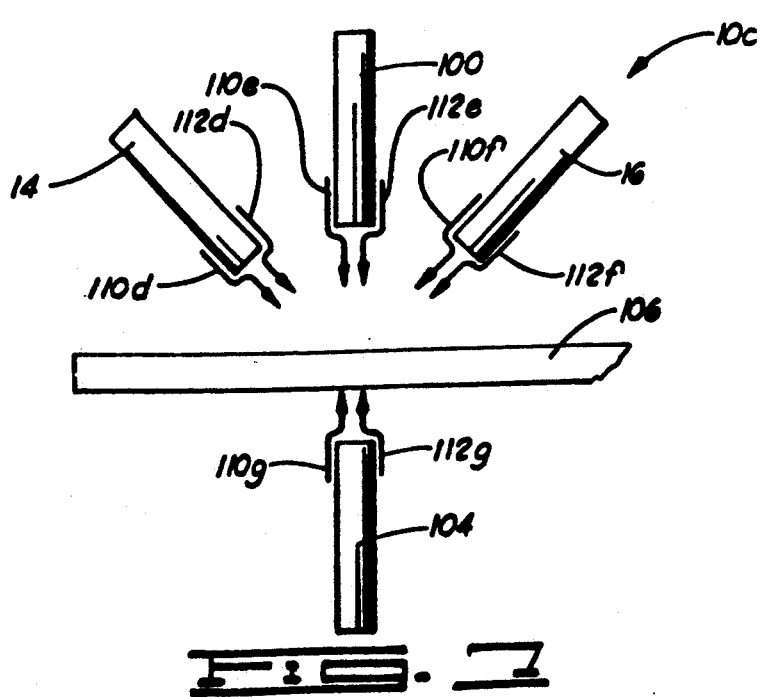
FIG. 7 is yet another system constructed in accordance with the present invention for nondestructively determining fiber volume fraction and resin porosity of composite materials.

Shown in FIG. 7 is another modified system 10c which is constructed in accordance with the present invention for nondestructively determining fiber volume fraction and resin porosity of a composite material, the composite material being diagrammatically shown in FIG. 7 and designated therein by the reference numeral 106. In this system 10c, the transducer 14 and the transducer 16 each are supported in a support plate (not shown) in a manner exactly like described before with respect to the system 10a shown in FIG. 6. Further, transducer 100 is supported in the support plate in a manner exactly like described before with respect to the system 10a shown in FIG. 6. Transducer 104 is supported so the second thickness transducer 104 is disposed and oriented with respect to the first thickness transducer 100 in a manner exactly like that described before with respect to the system 10a shown in FIG. 6.

In system 10c, a pair of water jets 112 are associated with each of the transducers 14, 16, 100 and 104. The water jets associated with the transducers 14, 16, 100 and 104 are schematically shown and represented in FIG. 7 by a pair of arrows associated with each transducer and designated by the reference numerals 110 and 112. The water jets associated with the transducer 14 are designated as 110d and 112d in FIG. 7, the water jets associated with the transducer 100 are designated 100e and 112e in FIG. 7, the water jets associated with the transducer 16 are designated 110f and 112f in FIG. 7 and the water jets associated with the transducer 104 are designated 110s and 112s in FIG. 7. The water jets 110 and 112 associate with each of the transducers are oriented to supply a jet of water generally between the end of the transducer and the surface of the composite material 106.

The water jets or streams provided by the water jets 110 and 112 provide a coupling for coupling the ultrasonic waves between the transducers and the composite material 10 thereby eliminating the need for immersing the transducers and the composite material in a reservoir containing the coupling agent as described before in connection with FIG. 6.

In this embodiment of the invention, the transducers 14, 16, 100 and 104 can be moved freely about the composite material 106. This embodiment of the invention permits the testing of large parts which are incapable of being immersed practically in a reservoir.

In this embodiment of the invention, the fiber volume fraction and resin porosity of the composite material are determined by the processor 26 in a manner exactly like that described before with respect to the system 10a shown in FIG. 6.

The procedures prescribed in detail before assume the state of cure of the composition material is known and therefore the elastic modulii of the constituent materials also are known. The elastic moduli of the constituent materials of the composite material vary with the state of cure and, where the state of cure is not known, procedures must be effected to measure the effect of the cure reaction in the composite material. Preferably, the procedures are compatible with ultrasonic sound measurements. In general, dielectric property measurements (conductivity, capacitance, permitivity, loss factor) can be used to accomplish this purpose.

Since ionic mobility is directly related to the extent of polymerization, measurement of conductivity can be correlated to the degree of cure. Hence, mechanical properties (Young's modulus, shear modulus, Poisson's ration, viscosity, etc.). It should be pointed out that these correlations are empirical and must be done for each resin system under consideration. See Marvin Bramm Berg, David Day, Huan Lee and Kimberly Russell "New Applications For Dielectric Monitoring and Control In advanced Composites: The Latest Developments", Published by American Society of Metals (1986, pages 307-311). These relationships are the basis for the present method of compensating for local variations in the extent of cure. It should also be mentioned that low frequency probes must be used for accurate cure measurements.

Initially, what is sometimes referred to herein as a "state of cure data base" is accumulated. Sample composite materials, each having the same constituent material as the composite material to be tested and each having a known state of cure, initially are established. Each of these sample composite materials is cured to various known states of cure, such as ten percent (10%) cured, twenty percent (20%) cured . . . one hundred percent (100%) cured, for example. The elastic moduli (shear and Young's moduli for example) and the dielectric property (e.g. conductivity) of each of these resin samples then is determined.

From this set of experimental or empirical data, curves plotting two independent elastic moduli such as shear and Young's versus conductivity for each of the sample composite materials are developed. These curves comprise the state of cure data base which is inputted into the processor 26. In a more preferred form, a formula is developed representing each of these curves and these formulae comprise the state of cure data base which is inputted into the processor 26. In either case, the state of cure data base is inputted into and stored in the processor 26.

The dielectric property measuring device outputs a signal which is indicative of the conductivity of the composite material to be tested.

Dielectric property devices which are capable of providing an output proportional to the capacitance of the composite material to be tested are well known in the art and one such device which can be used in the present invention is commercially available from Micromet Instruments, Inc., Eumetric System II.

The dielectric constant indicating device outputs an indication of the dielectric constant of the composite material being tested, and this output is digitized and inputted into the processor 26. Where the dielectric constant indicating device more particularly outputs an indication of the conductivity of the composite material to be tested, the processor 26 is programmed to determine the dielectric constant of the material to be tested from the inputted indication of measured conductivity.

The processor 26 has stored therein the state of cure data base, and the processor 26 is programmed to determine the shear modulus and the Young's modulus from the inputted output of the dielectric constant indicating device either from the curves stored in the state of cure data base or the formula stored in the state of cure data base.

After determining the required elastic modulii, the processor 26 then determines the other composite material parameters in the manner described before, but using the shear modulus and the Young's modulus determined in the manner just described.

With respect to the device as shown in FIGS. 6 and 7, the dielectric constant indicating device cannot be incorporated with the other transducers since water is used as the transmitting medium. In these cases, the dielectric constant indicating device which provides an output of the capacitance of the composite material being tested cannot be used in a water medium. In these instances where water is used as a transmitting medium, the dielectric constant indicating device separately is utilized to determine the dielectric constant of the composite material being tested.

Further, with respect particularly to the embodiment shown in FIGS. 6 and 7, it should be noted that the state of cure may, and in many instances will, vary over the area of composite material being tested. For example only, the state of cure along the edges of the composite material may be quite different as compared to the state of cure over the central portion of the composite material to be tested. The dielectric property of the composite material to be tested is determined at a plurality of points over the entire area of the composite material to be tested and the determined dielectric property are correlated with the other measured parameters for determining the parameters in accordance with the present invention.

EMBODIMENT OF FIGS. 8-17

Advanced fiber reinforced composite materials have seen widespread use in automotive and aircraft industries. Advanced fiber reinforced composites are materials with high strength and stiffness. In advanced fiber reinforced composite materials, the manufacturing process plays an important role in achieving the desired strength and material properties than in most conventional materials. Fiber reinforced composites can be grouped into thermoplastic materials and thermoset materials. Thermoplastic composites having reinforcing fibers (continuous or short fibers) in a resin matrix are manufactured either by a molding method like compression or injection molding, or by an extrusion method lime pultrusion. The manufacture of fiber reinforced thermoset composite consists of assembling the fiber and the matrix to make the lamina. Fibers are saturated with resinous material which subsequently is cured to form the matrix material of the composite structure. This process is referred to as pre-impregnation and such forms of pre-impregnated fibers are called "prepregs". These prepregs are used to make composite laminates.

With the increased use of structural composites to avoid laminate failure, it is necessary to improve prepreg processability characteristics and minimize laminate property variation. It has been found that a very subtle change in the cure state of the resin and in the prepreg properties caused production laminates to become unacceptably porous and to fill with inter laminar voids. This porosity variation can remain undetected during manufacture and becomes apparent only during the processing of the prepregs. Variations in the physical composition of the resin matrix can also affect the processability of the prepreg system as well as the properties of the finished part.

The fibers in a prepreg are randomly spaced in the transverse plane at an average fiber to fiber distance uniquely determined by the volume fractions of the fibers and the matrix. The stiffness and the strength properties of the composite depends on this internal packing geometry of the fibers and the constitutive behavior of the fiber and the matrix. Since the structural integrity of the composite material depends on the quality of the prepregs used, it makes it essential to control material defects which occur during prepreg manufacture. The present invention provides a cost effective nondestructive method for an on line quantitative evaluation of prepregs.

The present method and apparatus provides a nondestructive technique based on ultrasonic velocity measurement for an automatic on line quantitative characterization of microstructural prepreg properties. The present system provides a determination of fiber volume fraction and porosity in a composite prepreg on an on line production environment. A computer controlled composite prepreg rolling mill (FIG. 15-18) is utilized to facilitate on line prepreg testing. Prepregs are rolled, while being scanned by ultrasonic transducers set up in pitch catch mode inside the rolling mill. A software interface is interposed between the rolling mill and the computer, such as an Intel 90386 based personal computer, to control the speed, acceleration of the rollers and the distance travelled by the prepreg material.

The coupling between the roller and the prepreg material is utilized to measure transit time. To ensure accurate transit time prediction analytic signal magnitude developed by P. M. Gammel, "Improved Ultrasonic Detection Using The Analytical Signal Magnitude", Ultrasonics, 1981, pp 73–76 (such article being specifically incorporated herein by reference), is used. An algorithm is used to determine the fiber volume fraction and porosity of the prepreg given the material properties and the measured wave velocities. A software interface is interposed between the personal computer and digitizer, which allows data sampling and acquisition at 100 Mhz. All the above algorithms have been integrated into a user friendly software on the computer, (Intel 80386 based personal computer). This software allows for an on line automatic quantitative material characterization of prepregs in a production environment.

To develop a system for quantitative measurement of microstructural properties, the relationship between the microstructure and the material properties has to be established. This constitutes the micromechanics of composite materials which are based on elasticity theories. Therefore an appropriate micromechanics model has to be developed for the prepregs.

A micromechanics model is needed in order to take into effect the presence of pores in the resin. The pores are assumed to evenly distributed, spherical and microscopic. The model used was developed by S. Boucher, "On The Effective Moduli Of Isotropic Two Phase Elastic Composites", Journal Of Composite Materials, 18, 1974, pp 82–89, which was based on the expression for the strain field within a spherical inclusion derived by J. D. Eshelby, "The Determination Of The Elastic Field In An ellipsoidal Inclusion And Related Problems", Proceedings Of Royal Society, 241, Series A, 1957, pp 376–380, and the continuity of the strain field at the boundary of the inclusion. The modified matrix properties are given below.

$$G_S = \frac{G_m(9K_m + 8G_m)}{G(K_m + 2G_m)} \tag{7}$$

$$G^* = G_m \left( 1 - \frac{V_p}{1 - \left( \frac{G_m}{G_m + G_g} \right)} \right)$$

-continued $$K^* = K_m \left( 1 - \frac{V_p}{1 - \left( \frac{K_m}{K_m + \frac{4}{3} G_m} \right)} \right)$$

$$\rho^* = \rho_m(1 - V_p)$$

$$K^t = K^* + \frac{G^*}{3}$$

where
$G_m$-Shear modulus of the matrix,
$G^*$-Modified shear modulus,
$K_m$-Bulk modulus of the matrix,
$K^*$-Modified bulk modulus,
$\rho_m$-Density of the matrix,
$\rho^*$-Modified density,
$V_p$-Volume fraction of pores,
$K^t$-Modified transverse bulk modulus.

Using elasticity, one can derive the modified young's modulus and poissons ratio as follows.

$$E^* = \frac{9G^*K^*}{3K^* + G^*} \quad (8)$$

$$\nu^* = \frac{3K^* - 2G^*}{6K^* + 2G^*} \quad (9)$$

A micromechanics model is also needed to determine the stiffness coefficients of the unidirectional prepreg which constitutes of graphite fibers impregnated in epoxy resin. The following expressions and bounds for the elastic moduli of an unidirectional laminae consisting of transversely isotropic fibers and isotropic matrix were derived by Z. Hashin and B. W. Rosen, "The Elastic Moduli Of Fiber Reinforced Materials", Journal Of Applied Mechanics, Vol. 31 (1964), pp 223-232, on the basis of analogies between isotropic and transverse isotropic elasticity equations. By incorporating the modified matrix properties it is possible to calculate the effective moduli of a laminae given the fiber properties and the volume content of the fibers. In the formulas given below the subscripts m and f indicated matrix and fiber respectively. The subscript a indicates axial direction and subscript t indicates transverse direction (i.e.; perpendicular to the fiber direction).

$$K = K_m + \frac{V_f}{\frac{1}{K_f - K_m} + V_m K_m + G_m} \quad (10)$$

$$G_a = G_m + \frac{V_f}{\frac{1}{G_{af} - G_m} + \frac{V_m}{2G_m}}$$

$$E_a = E_m V_m + \frac{4(\nu_{af} - \nu_m)^2 V_m V_f}{\frac{V_m}{K_f} + \frac{V_f}{K_m} + \frac{1}{G_m}}$$

$$\nu_a = \nu_m V_m + \nu_{af} V_f + \frac{(\nu_{af} - \nu_m)\left(\frac{1}{K_m} - \frac{1}{K_f}\right) V_m V_f}{\frac{V_m}{K_f} + \frac{-V_f}{K_m} + \frac{1}{G_m}}$$

$$\rho = \rho_m + V_f(\rho_f - \rho_m)$$

where $V_f$—Fiber Volume fraction,
$V_m$—Modified matrix volume fraction.

K is the transverse bulk modulus. The transverse shear modulus of the laminae is dependent on the relationship between the transverse shear modulus of the fiber and matrix, and on the relationship between the bulk modulus of the fiber and the matrix as shown below.

$$G_t = G_m + \left( \frac{V_f}{\frac{1}{G_{tf} - G_m} + \frac{K_m + 2G_m}{2G_m(K_m + G_m)} V_m} \right) \quad (1)$$

The above equations can be used to determine the engineering coefficients of a laminae given the fiber volume fraction, porosity and the material properties.

The above engineering constants can be converted into stiffness coefficients a fourth order tensor $C_{ijkl}$ for the laminae. By using the symmetry considerations in stress and strain tensor, we can reduce the number of independent constants from 81 to 21. Further simplification can be achieved by using the following notation.

$11 \rightarrow 1, 22 \rightarrow 2, 33 \rightarrow 3, 23 \rightarrow 4, 13 \rightarrow 5, 12 \rightarrow 6$ Hence the stiffness coefficients for a laminae with fibers oriented along the axis is given by a symmetric 6×6 matrix as shown below.

$$\begin{bmatrix} C_{11} & C_{12} & C_{13} & 0 & 0 & 0 \\ C_{12} & C_{11} & C_{13} & 0 & 0 & 0 \\ C_{13} & C_{13} & C_{33} & 0 & 0 & 0 \\ 0 & 0 & 0 & C_{44} & 0 & 0 \\ 0 & 0 & 0 & 0 & C_{44} & 0 \\ 0 & 0 & 0 & 0 & 0 & \frac{C_{11} - C_{12}}{2} \end{bmatrix} \quad (12)$$

$C_{11} = K + G_t$ $C_{12} = K - G_t$ $C_{13} = 2\nu_a K$ $C_{22} = C_{11}$ $C_{23} = C_{13}$ $C_{33} = E_a + 4K\nu_a^2$ $C_{44} = G_a$ $C_{55} = C_{44}$ $C_{66} = G_t$

The basic governing equations for elastic wave propagation through a material can be derived from the equation of motion for a continuum, with no body forces as $$\rho \ddot{u}_i = \sigma_{ij,j} \quad (13)$$

where
$\rho$-Density,
$\ddot{u}$-Particle displacement,
$\sigma_{ij}$-Stress tensor.

Assuming a linearly elastic constitutive equation for the material $$\sigma_{ij} = C_{ijkl}\epsilon_{kl} \tag{14}$$

Substituting equation 14 into equation 13, $$\rho \ddot{u}_i = C_{ijkl}\epsilon_{kl,j} \tag{15}$$

The strain displacement relationship (assuming small displacements) is given below.

$$\epsilon_{kl} = \tfrac{1}{2}(u_{k,l} + u_{l,k}) \tag{16}$$

It is possible to rewrite equation 15 as $$\rho \ddot{u}_i = C_{ijkl} u_{k,lj} \tag{17}$$

Assuming a plane wave solution, the displacements can be written as $$u_i = A_o \alpha_i e^{[k(lx) - \omega t]_{lm}} \tag{18}$$

where
- $A_o$—Displacement amplitude,
- $\alpha_1$—Particle displacement direction cosiness,
- k—Wave number,
- $l_i$—Wave propagation direction cosiness,
- t—Time,
- $\omega$—Frequency,
- $x_1$—Distance from the coordinate axis.

Substituting equation 18 into equation 17 yields an eigen value equation of the form $$\rho \omega \alpha_i = C_{ijkl} k^2 l_j l_l \alpha_k \tag{19}$$

$$(C_{ijkl} l_j l_l - \rho v^2 \delta_{ik}) \alpha_{ik} = 0 \tag{20}$$

where $v = \omega/k$ is the phase velocity of the propagating wave. The above equation 20 can be rewritten as $$|C_{ijkl} l_j l_l - \rho v^2 \delta_{ik}| = |\lambda_{ik} - \rho v^2 \delta_{ik}| \tag{21}$$

where $$\lambda_{ik} = C_{ijkl} l_j l_l \tag{22}$$

Figure 8:
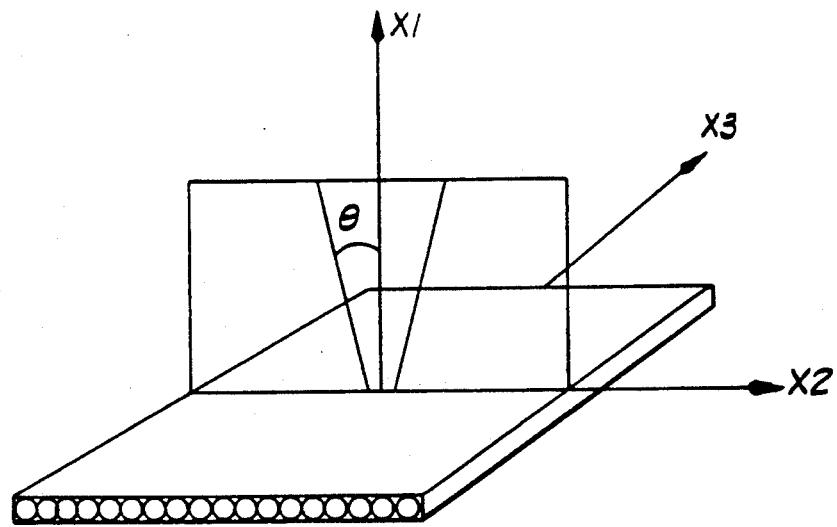
FIG. 8 is a diagrammatical illustration of wave propagation in prepreg.

An ultrasonic wave propagating through the prepreg material is as shown in the FIG. 8. The direction cosines for this wave are given below.

$$\begin{pmatrix} -\cos\theta \\ \sin\theta \\ 0 \end{pmatrix} \tag{23}$$

Expanding equation 22, $$\lambda_{11} = C_{11} \cos^2\theta + C_{66} \sin^2\theta \tag{24}$$

$$\lambda_{12} = -(C_{12} + C_{66}) \cos\theta \sin\theta$$

$$\lambda_{13} = 0$$

$$\lambda_{22} = C_{66} \cos^2\theta + C_{22} \sin^2\theta$$

$$\lambda_{23} = 0$$

$$\lambda_{33} = C_{55} \cos^2\theta + C_{44} \sin^2\theta$$

Substituting the value of $\lambda_{ik}$ in equation 21, $$\begin{vmatrix} \lambda_{11} - \rho v^2 & \lambda_{12} & 0 \\ \lambda_{12} & \lambda_{22} - \rho v^2 & 0 \\ 0 & 0 & \lambda_{33} - \rho v^2 \end{vmatrix} = 0 \tag{25}$$

The solution of equation of motion indicates that there are three possible velocity of propagation through the material which can be obtained by determining the eigen values and eigen vectors of equation 25. These are given below.

$$v_1 = \sqrt{\frac{C_{11}}{\rho}} \tag{26}$$

$$v_2 = \sqrt{\frac{C_{66}}{\rho}}$$

$$v_3 = \sqrt{\frac{C_{44}}{\rho}}$$

ULTRASONIC SIGNAL PROCESSING

The ultrasonic signals generated are used to predict the ultrasonic wave velocity through the material. The time required by the wave to travel through the material and back is measured. The ultrasonic velocity is the ratio between the distance traveled by the wave to the transit time.

Several methods are available to predict ultrasonic velocity based on the mode of transit time measurement, J. Krautkramer and H. Brautkramer. In this work analytical signal magnitude developed by P. M. Gammel, P. M. Gammel "Analogue Implementation Of Analytic Signal Processing For Pulse Scho Systems:, Ultrasonics, pp 279-283, 1981, is used to measure time delay. This technique is employed because of its superior resolvability of two closely spaced interfaces. With this technique the envelope of the ultrasonic signal is obtained by the calculation of the magnitude of the analytic signal.

When treating an ultrasonic signal as an analytic signal, the real signal is replaced by its complex form. For a simple harmonic function, the real signal is represented by $$f(t) = a \cos \omega t + b \sin \omega t \tag{27}$$

This is replaced by $$h(t) = f(t) + g(t) \tag{28}$$

Here a and b are constants. The function g(t) is obtained from f(t) by replacing cos $\omega t$ by sin $\omega t$ and sin $\omega t$ by $-\cos \omega t$. Richard C. Heyser, "Determination Of Loudspeaker Arrival Times, Part III", Journal Of The Audio Engineering Society, pp 902-905, has shown that the square of the magnitude of the analytic signal is proportional to the rate of arrival of one of the components of energy, which may be kinetic energy, potential energy, or a linear combination of both. The square of the real signal will thus be zero at any instant when one of its component energies is zero, whereas the square of the analytic signal magnitude will only be zero when the total instantaneous energy is zero. Since analytic signal magnitude is directly related to the rate of energy arrival, it is the optimal estimator of interface location for echo signals commonly used in ultrasonic analysis.

The conventional rectification of the ultrasonic signal is replaced by computing the magnitude of the analytic signal. The detection scheme uses the magnitude of the analytic signal instead of rectification, produces a signal which is proportional to the square root of the rate of arrival of energy at the transducer. If the real part of the signal is recorded, then the imaginary part $V_i(t)$ can be obtained from the Hilbert transform as given below.

$$V_i(t) = \int_{-\infty}^{\infty} V_r(t) \pi^{-1} (t - t^*)^{-1} dt^* \tag{29}$$

This equation 29 represents a convolution of the signal with the kernel $1/(\pi t)$. By convolution theorem, convolution of two functions can be implemented in the frequency domain by the multiplication of their Fourier transforms. Therefore convolution of equation 29 can be performed in the frequency domain by multiplying the Fourier transform of $V_r(t)$ by $-i\,\text{sgn}(f)$ (where sgn (f)$=-1$ for $f<0$, $=1$ for $>=0$) and then applying an inverse Fourier transform to the product.

Figure 9:
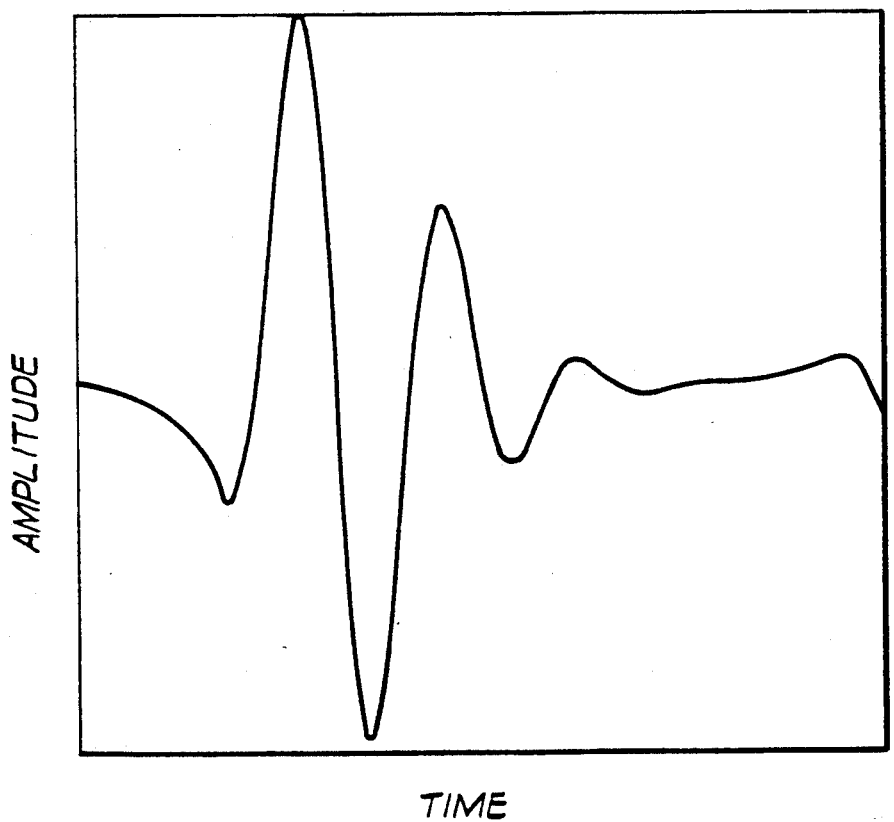
FIG. 9 is a graphical representation of a longitudinal wave.
Figure 10:
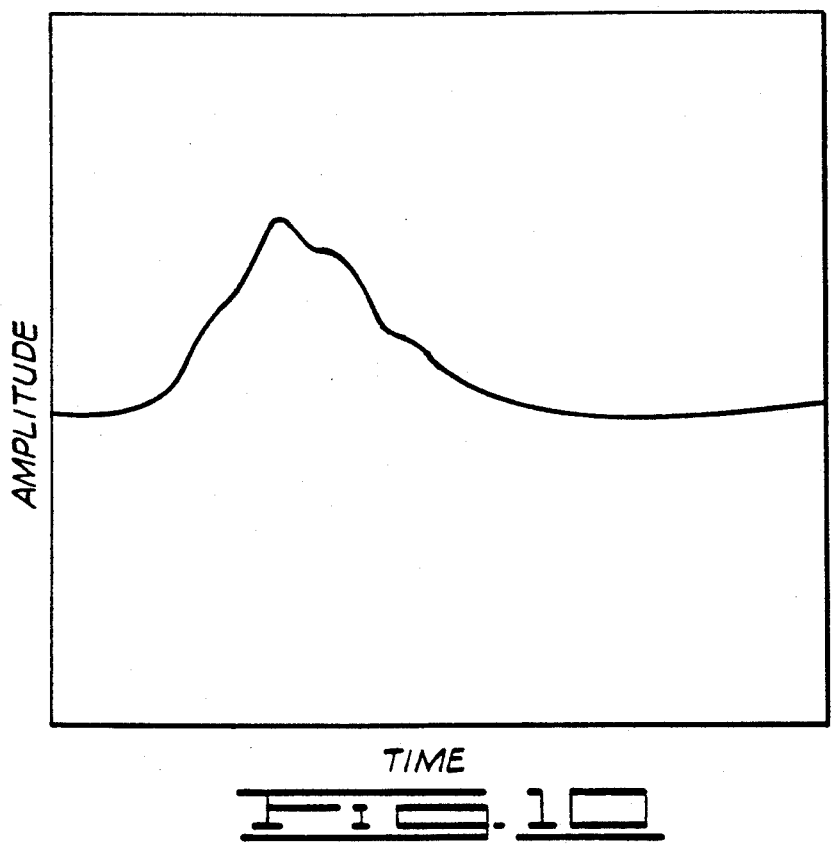
FIG. 10 is a graphical representation illustrating the analytical signal magnitude of a longitudinal wave.
Figure 11:
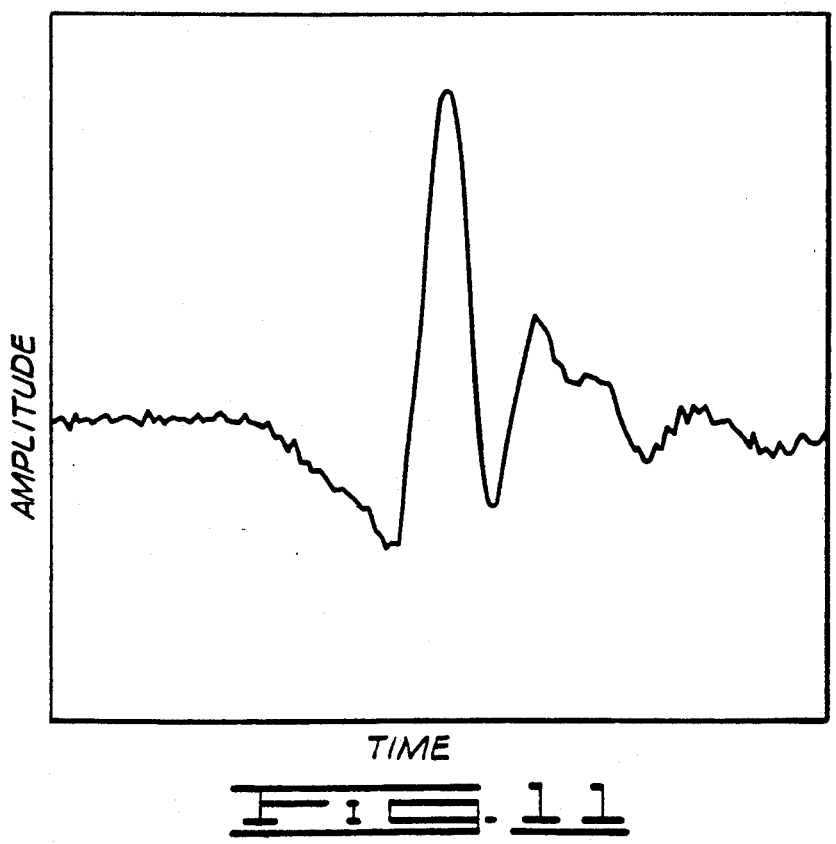
FIG. 11 is a graphical representation of a shear wave.

A complex fast Fourier transform algorithm is used which takes advantage of the symmetry properties of the Fourier transform of the analytic signals. The Fourier transform of the complex analytic signal can be obtained from the Fourier transform of one of its components by suppressing the negative frequency contributions. This means of obtaining the complex analytic signal consists of Fourier transforming the real signal by using a complex fft with imaginary part set equal to zero, then setting all negative frequency contributions to zero, and then taking an inverse fft which produces the real and imaginary parts of the complex analytic signal. With the full analytic signal available its magnitude may be calculated as the square root of the sum of the squares of the real and the imaginary part at each point in time. The analytic signal magnitude can then be used to produce a better A mode display. This improved A mode display is used in transit time calculations. FIG. 9 shows the ultrasonic signal of the longitudinal wave. FIG. 10 shows the analytical signal magnitude which clearly shows the interface between the roller and the prepreg. FIG. 11 shows the ultrasonic signal of the shear wave. FIG. 12 shows the analytical signal of the shear wave, from which the roller prepreg interface is clearly visible.

VELOCITY MEASUREMENT

FIG. 13 shows the experimental geometry for generating and receiving a longitudinal wave. The longitudinal wave velocity can be calculated as follows.

$$c_1 = \frac{2d}{\Delta t} \tag{30}$$

where
 d —Thickness of the prepreg,
 $\Delta t$ —Difference in time for the signal to be reflected from the prepreg and the roller back surface.

The measurement of shear velocity is slightly complicated. FIG. 14 shows the experimental geometry for generating and receiving a shear wave. The time taken for the signal to be reflected from the back surface of the roller is $\Delta t_1$ and the time taken for the signal is $\Delta t_2$.

The transit time for the signal is $\Delta t$ which is given below.

$$\Delta t = \Delta t_2 - \Delta t_1 \tag{31}$$

$$\Delta t = \frac{2 L_2}{V_x} - \frac{\Delta}{V_w} \tag{32}$$

Using the following relationships $$L_2 = \frac{d_2}{\cos \theta_{rr}} \tag{33}$$

and $$x = d_2 \tan \theta_{rr} \tag{34}$$

Equation 32 can be rewritten as $$\Delta t = \frac{2 d_2}{V_c \cos \theta_{rr}} - \frac{2 d_2 \sin \theta_{rr} \sin \theta_i}{V_w \cos \theta_{rr}} \tag{35}$$

Using Snell's law, $$\frac{\sin \theta_i}{V_w} = \frac{\sin \theta_r}{V_r} = \frac{\sin \theta_{rr}}{V_c} \tag{36}$$

From which, $$\sin \theta_{rr} = \frac{V_c}{V_w} \sin \theta_i,\ \cos \theta_{rr} = \sqrt{1 - \left(\frac{V_c \sin \theta_i}{V_w}\right)^2} \tag{37}$$

Substituting equation 38 into equation 35, $$\Delta t = \frac{2 d_2}{\sqrt{1 - \left(\frac{V_c \sin \theta_i}{V_w}\right)^2}} \left[\frac{1}{V_c} - \frac{V_c \sin \theta_i^2}{V_w^2}\right] \tag{38}$$

Rearranging equation 38, $$\Delta t = \frac{2 d_2}{V_c} \sqrt{1 - \left(\frac{V_c \sin \theta_i}{V_w}\right)^2} \tag{39}$$

Solving equation 39 for $V_c$ gives $$V_c = \frac{2 d_2}{\sqrt{[\Delta t]^2 + \left[\frac{2 d_2 \sin \theta_i}{V_w}\right]^2}} \tag{40}$$

ACID DIGESTION

The volume fractions of the constituents of a composite can be determined by chemical matrix digestion Leif A. Carlsson and R. Byron Pipes, "Experimental Characterization Of Advanced Composite Materials", Prentice Hall Publishing Co., N.J., 1987. This is a destructive procedure consisting of weighing the sample, dissolving it in concentrated nitric acid, drying and weighing the fibers and using the following formulae to calculate the volume fraction of the constituents.

$$V_f = \frac{\rho_m W_f}{\rho_f W_m + \rho_m W_f} \qquad (41)$$

where
$\rho_m$—Density of the matrix,
$\rho_f$—Density of the fiber,
$W_f$—Weight of the fiber,
$W_m$—Weight of the matrix.
which are all known quantities.

The results of the previous analysis are used in the algorithm to calculate the fiber volume fraction and porosity of the prepreg.

The most widely used manufacturing processes for graphite epoxy prepregs are hot melt process and solvent extraction process. In these processes, the pre-impregnated fiber with the resin is rolled between a series of rollers.

In hot melt process, the graphite fibers commercially available as tows are taken from a series of spring loaded spools and passed through a guiding plate and then through a comb which aligns the fiber on the horizontal plane. These fibers get sandwiched between resin coated paper and the entire material fed through a series of rollers. The resin gets partially cured by the hot water circulating inside the rollers. The resin paper on the top side of the prepreg is removed and the remaining prepreg material goes to a take up roller.

In the solvent extraction process, time graphite fibers are woven into a cloth like material and stored in rollers. The woven fibers are taken through a resin bath and fed through a series of rollers in a furnace, where the resin gets partially cured. Then the prepreg material is stored on take up rollers.

Shown in FIGS. 15, 16, 17 and 18 is an apparatus for non-destructively determining fiber volume fraction and resin porosity of a composite material or prepreg wherein the following parameters of the composite material or prepreg to be tested are known: density, elastic modulii of the constituent materials and layup sequence. The apparatus is adapted to non-destructively determine the parameters in an on-line testing application.

The apparatus basically consists of a cylindrically shaped roller 300 (FIGS. 15 and 16), a cylindrically shaped roller-transducer housing 302 (FIGS. 15, 16 and 17), a support 304 (FIGS. 15 and 16) for rotatingly supporting the roller 300 and the roller-transducer housing 302, a motor 306 for drivingly rotating at least one of the roller 300 and the roller-transducer housing 302, a transducer assembly 308 for propagating acoustic waves through the composite material or prepreg, water 309 disposed in the roller-transducer housing 302 to provide a medium through which the acoustic waves may be propagated, a computer 310 (FIG. 18) for controlling the transducer assembly 308 and the motor 306 and for processing the signals received from the transducer assembly 308 to determine the fiber volume fraction and resin porosity of the composite material or prepreg to be tested.

Figure 15:
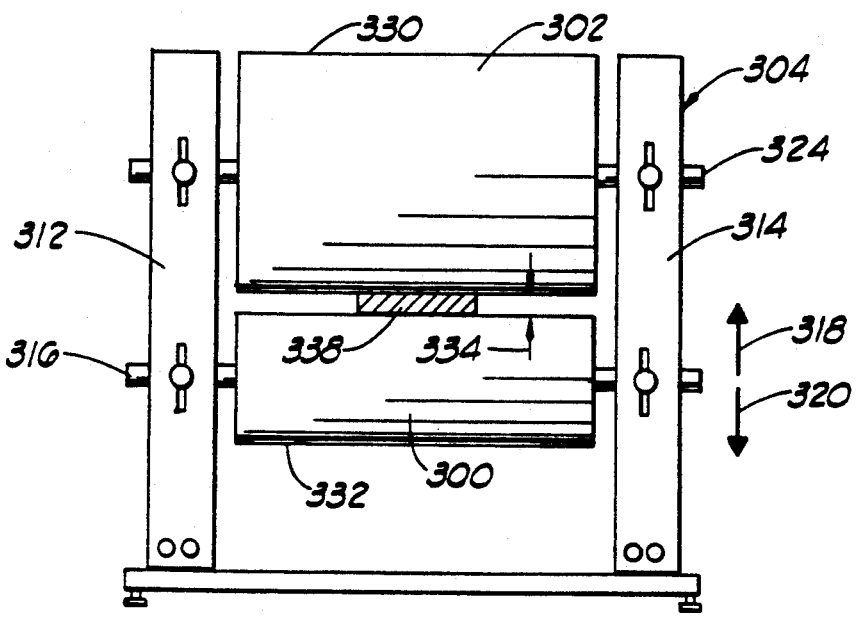
FIG. 15 is a front elevational view of an apparatus for measuring parameters of a prepreg in a continuous process.
Figure 16:
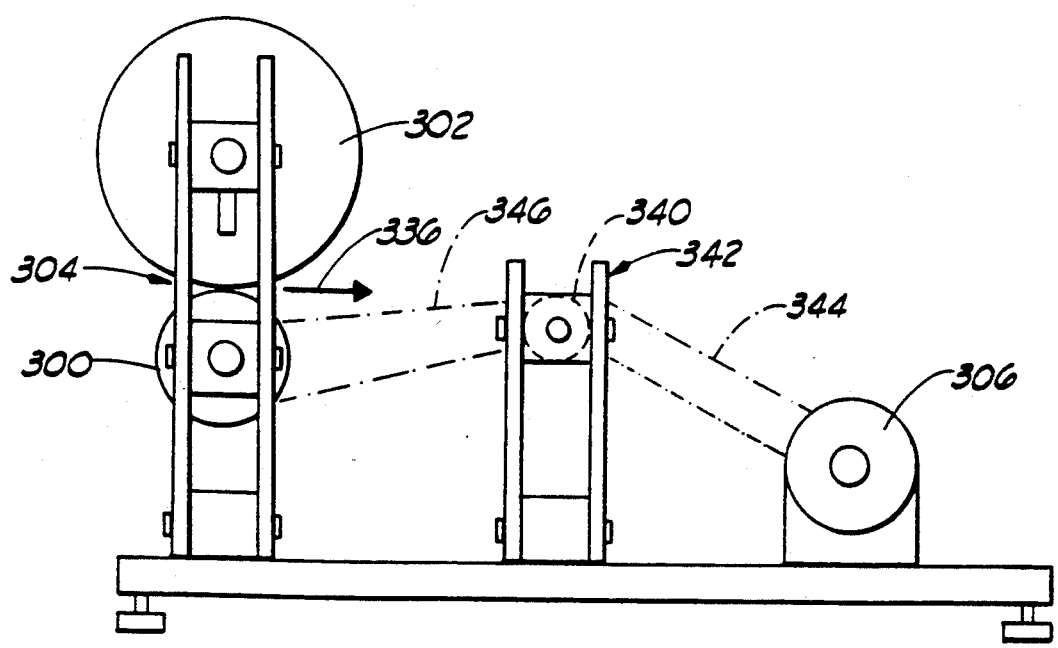
FIG. 16 is a side elevational view of the apparatus of FIG. 15.

The support 304 comprises a pair of spaced apart posts 312 and 314 (FIGS. 15 and 16). A shaft 316 (FIGS. 15 and 16) extends through the roller 300 and the roller 300 is secured to the shaft 316. One end of the shaft 316 is bearingly supported in the post 312 and the opposite end of the shaft 316 is bearingly supported in the shaft 314. The shaft 316 is supported in the posts 312 and 314 so that the shaft 316 and the roller 300 supported thereon can be moved in an upwardly direction 318 (FIG. 15) or a downwardly direction 320 (FIG. 15).

Figure 17:
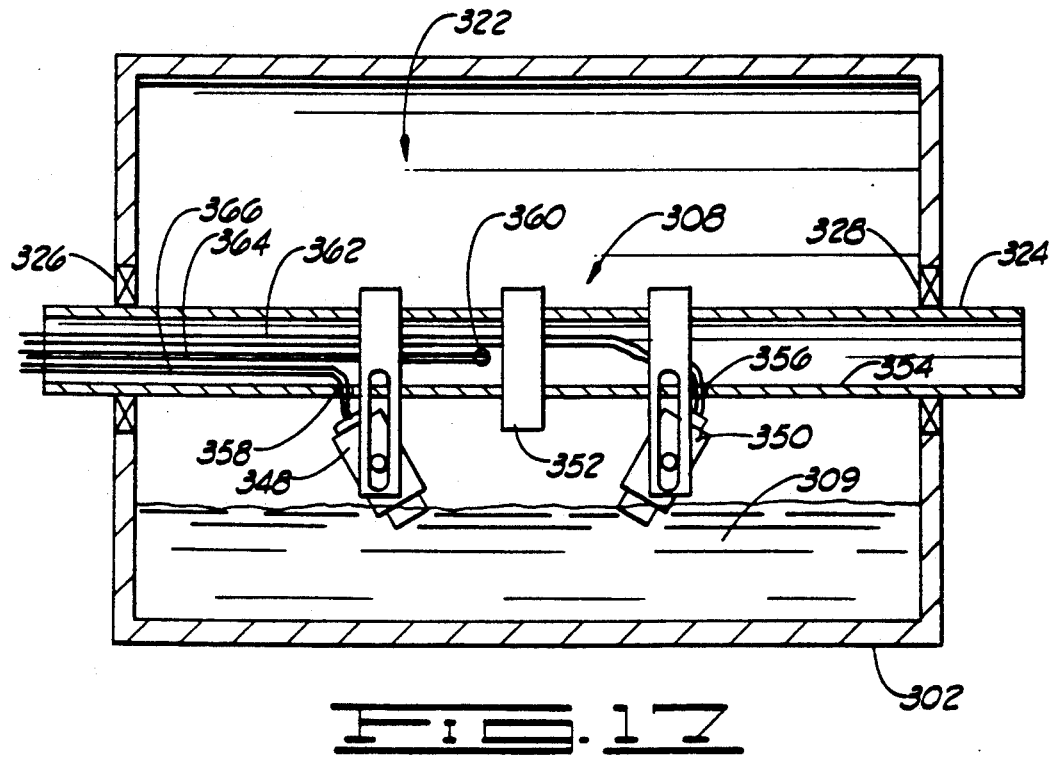
FIG. 17 is a sectional view of the roller-transducer housing of the apparatus shown in FIGS. 15 and 16.
Figure 18:
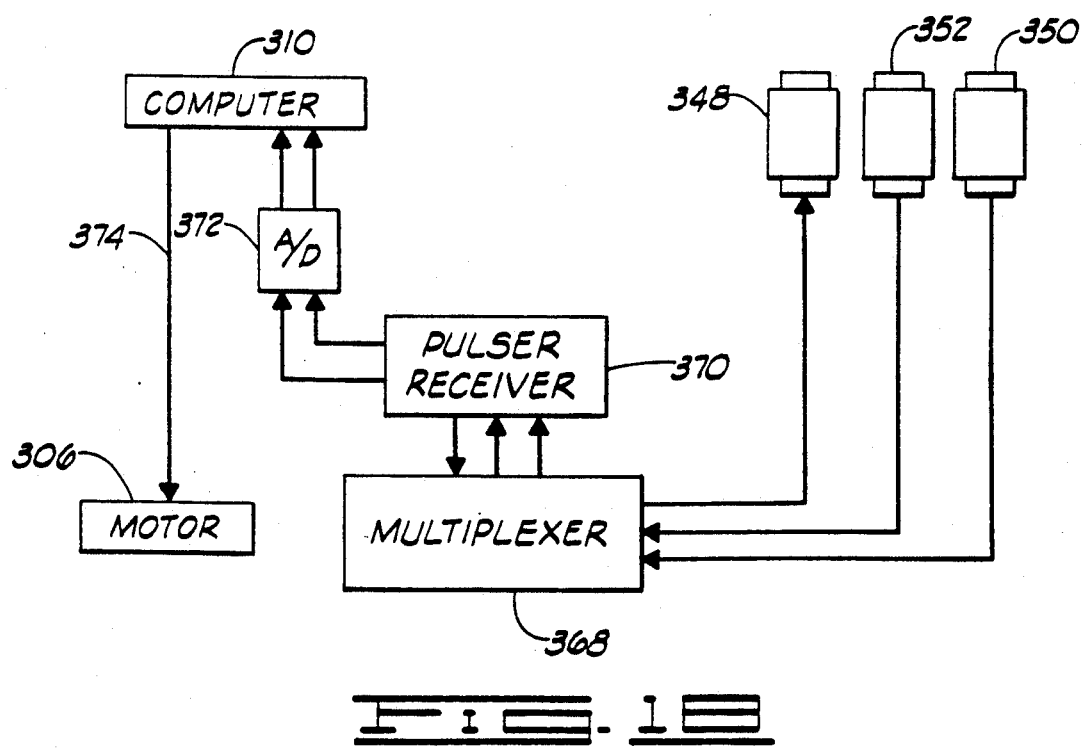
FIG. 18 is a schematic view of the system for determining the parameters using the apparatus of FIGS. 15 16 and 17.

The roller-transducer housing 302 is hollow and encompasses a component space 322 (FIG. 17). The water 309 is disposed in the component space 322. A shaft 324 (FIGS. 15 and 17) extends through the roller-transducer housing 302 and one end of the shaft 324 is secured to the post 312 and the opposite end of the shaft 324 is secured to the post 314 so that the shaft 324 is not rotatably supported on the posts 312 and 314. The roller-transducer housing 302 is bearingly connected to the shaft 324 by way of bearings 326 (FIG. 17) and bearing 328 (FIG. 17). Thus, the shaft 324 is non-rotatably supported by the support 304 while the roller-transducer housing 302 is rotatably supported on the shaft 324 for rotation about the shaft 324.

The roller-transducer housing 302 has an outer peripheral surface 330 (FIGS. 15 and 17) and the roller 300 has an outer peripheral surface 332 (FIG. 15). The roller 300 and the roller-transducer housing 302 are supported by the support 304 so that the outer peripheral surface 330 of the roller-transducer housing 302 is spaced a predetermined distance 334 from the outer peripheral surface 332 of the roller 300. The distance 334 is sized so that the outer peripheral surfaces 330 and 332 of the roller-transducer housing 302 and the roller 300, respectively, grippingly engage the composite material or prepreg disposed therebetween for moving the composite material or prepreg in an advance direction 336 (FIG. 16). The composite material or prepreg is shown in FIG. 15 and designated therein by the reference numeral 338.

A take-up roller 340 (FIG. 16) is rotatingly supported on a take-up roller support 342 (FIG. 16), only one end portion of the take-up roller support 342 being shown in FIG. 16 with the opposite end of the take-up support 342 being constructed exactly like the end shown in FIG. 16. When the roller 300 and the roller-transducer housing 302 are rotated, the composite material or prepreg 338 is moved in the advanced direction 336 a predetermined distance and the composite material or prepreg 338 is rolled onto the take-up roller 340. The take-up roller 340 was used in the test apparatus shown in FIGS. 15-18; however, in an actual on-line process, the prepreg may be advanced to another stage of processing rather than being taken up or rolled up on a roller such as the take-up roller 340.

The output shaft of the motor 306 is drivingly connected to the take-up roller 340 and to the roller 300 via chains 344 and 346 (FIG. 16).

The transducer assembly 308 comprises a shear wave generating transducer 348, a shear wave receiving transducer 350 and a longitudinal wave generating and receiving transducer 352. The shear wave generating transducer 348, the shear wave receiving transducer 350 and the longitudinal generating and receiving transducer 352 each are securedly fixed to the shaft 324. The shaft 324 is hollow and includes an opening 354 extending therethrough. The shaft 354 also includes openings 356, 358 and 360 for receiving cables from the respective shear wave generating transducer 348, the shear wave receiving transducer 350 and the longitudinal wave generating and receiving transducer 352, the cables being shown in FIG. 17 and designated by the respective reference numerals 362, 364 and 366. The cables 362, 364 and 366 form signal paths for connecting the transducers 348, 350 and 352 to the computer 310 via other components to be described below.

More particularly, the signals from the shear wave receiving transducer 350 and the longitudinal generating and receiving transducer 352 are passed through a multiplexer 368, a pulser receiver 370 and an analog to digital convertor 372 and processed in a manner like that described before with respect to the computer 26, the multiplexer 20, the pulser receiver 22 and the analog to digital converter 24 shown in FIG. 5.

In operation, the computer 310 outputs a signal on a signal path 374 which engages the motor 306 for drivingly rotatingly the roller 300 and the take-up roller 340. The roller 300 is rotatingly driven thereby moving the composite material or prepreg 338 in the advance direction 336. The computer 310 is programmed to maintain the motor 306 engaged for a predetermined period of time until the composite material or prepreg 338 has moved a predetermined distance in the advance direction 336. When the composite material prepreg 338 has been moved in the advanced direction 336 the predetermined distance, the computer 310 outputs the signal on the signal path 374 disengaging the motor 306 thereby stopping the rotation of the roller 300 and the roller-transducer housing 302. The computer 310 then causes the transducer assembly 308 to output the two independent acoustic waves (the shear wave and the longitudinal wave). The shear wave and the longitudinal wave are propagated through the water medium 309, through the thickness of the roller-transducer housing 302, through the prepreg or composite material 338 and the shear wave and the longitudinal wave then are reflected back and received by the transducer assembly 308. The propagation of the shear wave and the longitudinal wave through the water medium 309, the roller-transducer housing 302 and the composite material or prepreg 338 is illustrated in FIGS. 13 and 14. The shear wave and the longitudinal wave are received by the transducer assembly 308 and the transducer assembly 308 outputs the received waves through the multiplexer 368, pulser receiver 370 and the analog to digital convertor 372.

The computer 310 is programmed to determine the velocity of each of the two acoustic waves propagated through the composite material or prepreg 338 and determine the fiber volume fraction and resin porosity of the composite material and prepreg 338 using the determined velocities, the thickness and the known parameters of density, elastic modulii of the constituent materials and the layup sequence.

The thickness of the composite material maybe determined in a manner like that described before in connection with FIG. 5. However, in the manufacture of prepreg, the thickness of the prepreg at various stages commonly is determined and this thickness can be inputted into the computer without the necessity of having an independent thickness determination.

One operational, experimental model of the invention in accordance with FIGS. 15-18 was constructed and tested.

The following material HYE-1337AU tape used for test purposes was supplied by Fiberite, made of AS4 Graphite fibers and 937A Epoxy Resin. Proper care was exercised to ensure that the material remains fresh during the test process.

EXPERIMENTAL SETUP

The roller-transducer housing 302 was 12" in diameter, and the transducer assembly 308 was mounted inside this roller 302. The roller 300 was 4" in diameter. This roller 300 was connected to the take-up roller 340 by the chain drive. The take up roller 340 was 2" in diameter and was coupled to the stepper motor 306 by the chain drive. The rollers 300 and 302 were mounted rigidly by using vertical columns and bearing blocks (support 304). The shaft 324 in the roller-transducer housing 302 was made hollow on one side so that cables could be used to connect to the transducers 348, 350 and 352. Locking collars were used to prevent the axial motion of the rollers 300 and 302.

A slotted head grub screw was used in each of the bearing block to lock the shafts 316 and 324 in a normal position.

Programmable motion control was made possible by using a high accuracy 1.8 degree hybrid stepper motor. The stepper motor 306 took 12800 steps for one full revolution. Due to this, the distance travelled by the prepreg could be monitored accurately. Moreover, the speed and the acceleration of the rollers 300 and 302 could be set for the desired scanning rate. The stepper motor 306 was connected to the serial port of a Intel 80386 based personal computer 310. An user friendly software was developed which downloaded the appropriate commands to stepper motor 310, thereby ensuring a programmable rolling system. Typical commands issued for motion were "LD3 MN MPI A10 V0.1 D01024 G". Here, "LD3" disabled the motor 310 limit switches. "MN" was used for preset moves. "MPI" was used to set the motor 310 to incremental position mode. "A" was used to set the acceleration to 10 rev/sec$^2$ "V" was used to set the velocity to 0.1 revs/sec. "D" was used to set the distance moved to 1024 counts. Here, positive distance counts made a motion in the clockwise direction, while negative distance counts made a motion in the anti-clockwise direction. "G" was used as a go or make a move command. The program listing is given in Table I, at the end of the description.

The primary aim of the rolling mill was to scan the prepreg under manufacture on the production line. Ultrasonic transducers 348, 350 and 352 were mounted inside the roller 302. A Panametrics 2.24 Mhz transducer 352 was used to generate the longitudinal wave, while two panametrics 5 Mhz transducers 348 and 350 were used to generate the shear wave. The roller 302 was filled with water which acted as couplant to propagate ultrasonic waves. The distance 324 between the roller 302 and the driven roller 300 could be adjusted by moving the roller 300 vertically in the slot provided in the support 304. Once the roller gap was adjusted, the driven roller 300 could be locked in position by using the lock nuts and then the prepreg could be rolled and scanned.

The longitudinal and the shear transducers 348, 350 and 352 were connected to Panametrics pulser receivers. The incident angle for the shear transducers 348 and 350 in the pitch catch mode was set to 26 degrees. The choice of the incident angle was based on the observation that, if a wave propagates above the critical angle for aluminum, only a shear wave will be propagated in the roller 302. This eliminates multiple reflections from the back surface and also improves the signal resolution at the roller 302-prepreg 338 interface. The pulser receivers (only one being shown in FIG. 18 and designated 320) were connected to a Transiac 2001 digitizer (analog to digital convertor 372). A software interface to the digitizer 372 was developed for automatic digital data acquisition and sampling. The program listing is given in Table I, at the end of the description. The data signals were sampled at 100 Mhz, and analyzed on an Intel 80386 based personal computer 310. Analytical signal magnitude was performed on the received signal and a three point interpolation fit, D. M. Egle, "Using The Acoustoelastic Effect To Measure Stress In Plates", UCRL-52914, Lawrence Livermore Laboratory, 1980, was used to determine the peak point of the analytical signal. This improved the resolution of the signal to 5 ns. The wave velocities were measured in the manner described before. The algorithms described above were integrated to form the on line test device. Graphite epoxy prepregs 2" in width and 12" in length were scanned. To prevent the tacky prepreg material from sticking to the rollers 300 and 302, the surfaces were cleaned with a solvent like acetone. However proper care was taken to ensure that the solvent did not come in contact with the prepreg material.

ACID DIGESTION

Test specimens were made from 1.4" by 1.5" prepreg samples. The samples were weighed accurately, and dissolved in boiling concentrated nitric acid, so as to remove all the epoxy resin present in the prepreg. The remaining graphite fibers were washed, dried, and weighed accurately. The fiber volume fraction was calculated. The remaining acid was diluted, neutralized with baking soda and then it was disposed.

FIBER VOLUME FRACTION AND POROSITY PREDICTION

An algorithm was developed which used the time delay measurements to predict the fiber volume fraction and porosity in the prepregs. The following steps describe the algorithm.

1. Input the material properties of the matrix and fiber.
2. Input the wave velocities.
3. Calculate the modified matrix property, and hence calculate the prepreg stiffness.
4. Call the non linear equation solver with an initial guess for fiber volume fraction as 60% and porosity as 0%. Define a function which uses the difference between the measured wave velocity and the predicted wave velocity to optimize the fiber volume fraction and porosity for the measured velocities.

The program listing of the above algorithm is given in Table II, at the end of the description. The material properties used for the matrix and the fiber are given in Tables III and IV below.

The quantitative evaluation of the prepreg was done as mentioned before. The results are presented below.

TABLE III

| Matrix Material | 937A Epoxy Resin |
| --- | --- |
| Density $\rho_s$ | 1.2 gm/cc |
| Tensile Modulus $E_s$ | 5.35 Gpa |
| Poissons Ratio $\nu_m$ | 0.28 |

TABLE IV

| Fiber Material | AS4 Graphite Fibers |
| --- | --- |
| Density $\rho_s$ | 1.7 gm/cc |
| Tensile Modulus $E_s$ | 232 Gpa |

TABLE IV-continued

| Fiber Material | AS4 Graphite Fibers |
| --- | --- |
| Poissons Ratio $\nu_s$ | 0.278 |
| Shear Modulus $G_s$ | 30 Gpa |
| Shear Modulus $G_f$ | 5 Gpa |
| Bulk Modulus $K_f$ | 7.5 Gpa |

In the above experiments, a 45" long section of prepreg was analyzed. Twenty five ultrasonic measurements are made at 1.5" increments along the length of the prepreg. Twenty five specimens are analyzed by acid digestion. The specimens were cut as close as possible to the point that there is a variation in the thickness of the prepreg when it is rolled. The thickness of the prepreg was monitored by measuring the distance between the rollers by using a feeler gage.

Table V shows the measured ultrasonic wave velocities. Longitudinal velocity varies from 2572 m/s to 2753 m/s, while the shear velocity varies from 1695 m/s to 1816 m/s. The longitudinal velocity made by contact measurement is 2636 and the shear velocity made by contact measurement is 1690. The maximum variation in longitudinal velocity is about plus or minus 3.5%. The maximum variation in shear velocity is about plus 7%. The possible sources of error are given below.

TABLE V

| No | Longitudinal Velocity m/s | Shear Velocity m/s |
| --- | --- | --- |
| 1 | 2637.92 | 1695.23 |
| 2 | 2594.11 | 1702.98 |
| 3 | 2636.12 | 1748.75 |
| 4 | 2689.43 | 1790.91 |
| 5 | 2704.97 | 1778.6 |
| 6 | 2712.06 | 1802.62 |
| 7 | 2714.9 | 1812.55 |
| 8 | 2646.31 | 1750.29 |
| 9 | 2625.19 | 1712.81 |
| 10 | 2680.55 | 1780.44 |
| 11 | 2703.43 | 1785.33 |
| 12 | 2757.58 | 1778.28 |
| 13 | 2706.77 | 1808.17 |
| 14 | 2740.94 | 1759.18 |
| 15 | 2588.46 | 1703.36 |
| 16 | 2671.32 | 1770.25 |
| 17 | 2661.1 | 1763.95 |
| 18 | 2705.8 | 1784.55 |
| 19 | 2635.47 | 1739.53 |
| 20 | 2723.88 | 1816.15 |
| 21 | 2707.7 | 1800.25 |
| 22 | 2608.04 | 1717.26 |
| 23 | 2698.51 | 1787.26 |
| 24 | 2597.51 | 1707.31 |
| 25 | 2572.88 | 1714.35 |

1. Variation in thickness caused by non uniform rolling surface. The roller surfaces are not precisely machined. This causes small discrepancy in the thickness measured.
2. The fixtures used for aligning the transducers allowed manual adjustment of the transducer. Due to the coarseness of the mechanical fixture some error could be introduced here.
3. The data sampling rate used was 100 Mhz. This gives a signal resolution of 10 ns between successive data points. The time delays calculated from this signal resolution is not accurate enough, as any small variation can cause a large difference in velocity.
4. Signals digitized get distorted due to corrosion of metal parts inside the roller. This deposits on the bottom of the roller surface and gives rise to noise in the data.

Table VI below shows the fiber volume fraction as calculated from acid digestion, and the fiber volume fraction and porosity as calculated from ultrasonic measurements. The small variation in the fiber volume fraction can be attributed to the errors in the weighing process. Another source of error is fiber loss during acid digestion process, and also fiber weight loss due to fibers being subjected to attack by the hot nitric acid.

Table V compares the fiber volume fraction from the ultrasonic measurements and the fiber volume fraction from the chemical digestion process along the length of the prepreg. The graph show good correlation between the fiber volume fraction measured by acid digestion process and the fiber volume fraction calculated from the ultrasonic measurements.

It should be noted that, in an actual on line system, the transducer assembly 308 would be mounted to move axially along the shaft 324 so different points of the prepreg may be sampled along the width of the prepreg. In a preferred alternate, a plurality of transducer assemblies 308 would be connected to the shaft 324 for sampling at the various points along the width of the prepreg.

Changes may be made in the construction and the operation of the various components, elements and assemblies described herein without departing from the spirit and scope of the invention as defined in the following claims.

TABLE VI

| No | Fiber Volume Fraction (%) | | Porosity (%) |
|---|---|---|---|
| | Acid Digestion | Ultrasonic | |
| 1 | 46.09 | 42.75 | 0.00 |
| 2 | 49.77 | 48.10 | 2.85 |
| 3 | 50.15 | 50.37 | 2.20 |
| 4 | 47.38 | 50.33 | 0.54 |
| 5 | 47.57 | 49.17 | 0.00 |
| 6 | 51.1 | 50.39 | 0.00 |
| 7 | 51.32 | 50.97 | 0.00 |
| 8 | 48.1 | 49.29 | 1.58 |
| 9 | 46.54 | 45.76 | 1.20 |
| 10 | 50.63 | 49.79 | 0.65 |
| 11 | 49.67 | 49.42 | 0.00 |
| 12 | 50.4 | 50.81 | 0.00 |
| 13 | 50.76 | 50.85 | 0.16 |
| 14 | 51.07 | 49.47 | 0.00 |
| 15 | 47.1 | 48.91 | 3.21 |
| 16 | 47.81 | 49.33 | 0.80 |
| 17 | 49.11 | 49.62 | 1.22 |
| 18 | 47.3 | 49.46 | 0.00 |
| 19 | 51.69 | 48.91 | 1.81 |
| 20 | 49.9 | 51.41 | 0.00 |
| 21 | 51.36 | 50.20 | 0.00 |
| 22 | 46.45 | 48.73 | 2.59 |
| 23 | 46.94 | 49.35 | 0.00 |
| 24 | 46.9 | 48.37 | 2.81 |
| 25 | 50.97 | 52.93 | 4.47 |

TABLE I

```
/* Program to digitize ultrasonic signals */ include "scan.h"       /* file definitions */
main()
{
      int plc=1;
      int c1, c2, boo;
      int ndel1, ndel2;
      int avg1, avg2;
      float scale=1.0;
      float data[1024] ={0};
      float data1[1024] = {0};
      float data2[1024] = {0};
      int iMainCur = 0;
      int iCamcur = 0;

int graphdriver = DETECT, graphmode;
      if(registerbgidriver(EGAVGA_driver) < 0) exit(1);
      initgraph(&graphdriver, &graphmode, "");
      cmode = getgraphmode();

N=1; Q=0; X=0; DT=0;
      F=1; Crate_set(&F);
      F=64; Camcl(&F);
ten:
```

```
        row = 1; col = 1;

while( TRUE )
 {
   iMainCur = Menu( row, col, mnuMain, iMainCur );
    switch( iMainCur )
     {
case KMAC:
        row=1; col=1; setgraphmode(cmode);
        while(TRUE)
        {
             iCamcur = Menu(row,col,mnuCam,iCamcur);
             switch( iCamcur )
             {
             case CHA:
        cn = 2;
        boo = 0;
        break;
     case CHN:
        cn = 7;
        boo = 0;
        break;
     case BOT:
        c1 = 2;
        c2 = 7;
        boo = 1;
        break;

case WIO:
        box(); gotoxy(8,4);
        if(boo == 0)
        {
printf("Window Offset for Channel  %d :   ",cn);
        scanf("%d",&ndel);
        }
        else if(boo == 1)
        {
printf("Window Offset for Both Channels :");
        scanf("%d %d",&ndel1,&ndel2);
        }
        setgraphmode(cmode);
        break;
     case WIR:
        box(); gotoxy(8,4);
printf("Window Range :");
        scanf("%d",&npts);
        setgraphmode(cmode);
        break;
     case RL :
        box(); gotoxy(8,4);
printf("Record Length :");
        scanf("%d",&nrec);
        setgraphmode(cmode);
        break;
     case AV :
```

```
            box(); gotoxy(8,4);
            if(boo == 0)
            {
printf("# To Average for Channel %d :",cn);
            scanf("%d", &avg);
            }
            else if(boo == 1)
            {
printf("# To Average for Both Channels :");
                    scanf("%d %d",&avg1,&avg2);
                    }
                    setgraphmode(cmode);
                    break;
                case PS:
                    box(); gotoxy(8,4);
            printf("Plot Scale :");
                    scanf("%f",&scale);
                    setgraphmode(cmode);
                    break;
                case EX :
                    setgraphmode(cmode);
                    goto ten;
            }
        } case DIG:
    if(boo == 0)
    {
        display(data, cn, npts, nrec, ndel, avg);
    }
    else if(boo == 1)
    {
            display(data1, c1, npts, nrec, ndel1, avg1);
            display(data2, c2, npts, nrec, ndel2, avg2);
    }
    break;
case PLO:
    setgraphmode(cmode);
    if(boo == 0)
    {
            plot(data, npts, plc, scale, cn); getch();
    }
    else if(boo == 1)
    {
            plot(data1, npts, plc, scale, c1);
            plot(data2, npts, plc, scale, c2); getch();
    }
    plc = 1.0;
    setgraphmode(cmode);
    break;
case SIG:
    if(boo == 0)
    {
        asig(data);
    }
```

```
        else if(boo == 1)
        {
                asig(data1);
                asig(data2);
        }
        plc = 2.0;
        break;
case WR:
        box(); gotoxy(8,4);
        if(boo == 0)
        {
           printf("Data file name :");
           scanf("%s", &name);
              fp=fopen(name,"w");
           for(i=0; i<npts; i++)
              fprintf(fp,"%f\n",data[i]);
        }
        else if(boo == 1)
        {
           printf("Data file names (2 & 7) :");
           scanf("%s %s",&name1, &name2);
           fp=fopen(name1, "w");
           for(i=0; i<npts; i++)
            fprintf(fp,"%f\n",data1[i]);
           fpp=fopen(name2, "w");
           for(i=0; i<npts; i++)
            fprintf(fpp,"%f\n",data2[i]);
        }
        setgraphmode(cmode);
        break;
case TIM:
        setgraphmode(cmode);
        box1();
        if(boo == 0)
        {
        func_tim(data);
        gotoxy(8,4);
        printf("Channel No : %d",cn);
        gotoxy(8,8);
        printf("delta t is %d & time delay is %f",j-kk,fract);
        }
        else if(boo == 1)
        {
        func_tim(data1);
        gotoxy(8,4); printf("Channel No : %d",c1);
        gotoxy(8,6);
        printf("delta t is %d & time delay is %f",j-kk,fract);
        func_tim(data2);
        gotoxy(8,8); printf("Channel No : %d",c2);
        gotoxy(8,10);
        printf("delta t is %d & time delay is %f",j-kk,fract);
        }
        getch(); setgraphmode(cmode);
        break;
case FIB:
```

```c
            setgraphmode(cmode);
            status(spawnl(P_WAIT,pathname,args[0],args[3],NULL));
            setgraphmode(cmode);
            break;
        case BR:
            setgraphmode(cmode);
            status(spawnl(P_WAIT,path,args[1],args[3],NULL));
            setgraphmode(cmode);
            break;
        case MOT:
            setgraphmode(cmode);
            status(spawnl(P_WAIT,path1,args[2],args[3],NULL));
            setgraphmode(cmode);
            break;
        case QUIT:
            restorecrtmode();
            return FALSE;
        }
    }
}

/* function to digitize a signal using the camac board */ display(data, cn, npts, nrec, ndel, avg)
float data[];
{
    if(cn == 2)
        N=2;
    else if(cn == 7)
        N=7;
    for(i=0;i<=npts;i++) data[i]=0;

/* reset the module for sampling */

F=9; A=0; Camo(&N, &F, &A, &DT, &Q, &X);
    if(Q<1 || Q>1)
    {
        printf("Channel not responding");exit(1);
    }

/* generate stop trigger equivalent to front pannel */

F=25; A=0; Camo(&N, &F, &A, &DT, &Q, &X);

/* enable the lam */
    for(kk=0; kk<=avg; kk++)
    {
    F=26; A=0; Camo(&N, &F, &A, &DT, &Q, &X);
bp:

/* test the internal lam */

F=8; A=0; Camo(&N, &F, &A, &DT, &Q, &X);
    if(Q==0)
        goto bp;
```

```c
/* skip horizontal offset */ for(i=0; i<=ndel; i++)
    {
        F=2; A=0; Cami(&N, &F, &A, &DT, &Q, &X);
    }

/* read data sequentially */ for(i=0; i<=npts; i++)
    {
        F=2; A=0; Cami(&N, &F, &A, &DT, &Q, &X);
        if(Q==1 && i<=nrec)
            data[i] += DT;
    }

/* reset */

F=9; A=0; Camo(&N, &F, &A, &DT, &Q, &X);
    }
    for(i=0; i<=npts; i++) data[i]=data[i]/avg;
}

/* function to plot the signal */ plot(data, npts, plc, scale, cn)
float data[];
int plc;
float scale;
{
    int i, nn, skip;
    float ymax1, cost, ave, mag=498;
    float y1, y2, y3, aa1, aa2, x1, x2, a, a1;
    if(plc == 1)
    {
        cost = 0.0;
        for(i=0; i<npts; i++) cost += data[i];
        ave = cost/npts;
        for(i=0; i<npts; i++) data[i] = data[i] - ave;
    }
    ymax1 = data[0] ; nn = npts;
    for(i=1; i<nn; i++)
    {
        if(data[i] > ymax1) ymax1 = data[i];
    }
    for(i=0; i<nn; i++) data[i] *= -1;  /* to invert the
                                           screen coord */
    lowvideo(); setcolor(11);
    rectangle(50,20,580,460);
    rectangle(54,24,576,456);

line(70,30,70,450);         /* y axis */
    line(70,140,570,140);       /* x1 axis */
    line(70,230,570,230);       /* co-ord axis */
```

```
line(70,360,570,360);      /* x2 axis */ settextstyle(SMALL_FONT, HORIZ_DIR, 5);
setcolor(3);
outtextxy(280,210,"CHANNEL 2");
outtextxy(280,440,"CHANNEL 7");

a=nn/10; a1=a; aa1=nn/10; aa2=aa1;

if(cn == 2)
     skip = 140;
else if(cn == 7)
     skip = 360;
moveto(70,skip);            /* go to 0,0 */
setcolor(12);

for(x1=0; x1<nn; x1++)
{
     y1=data[x1]*(scale*100/ymax1);
     y1 += skip;
     x2=70+(mag/nn)*x1;
     lineto(x2, y1);
}
for(x1=0; x1<nn; x1++)
{
     x2=70+(mag/nn)*x1;
     if(x1 == a1)
     {
          setcolor(15);
          line(x2,225,x2,235);
          itoa(aa1,abc,10);
          settextstyle(SMALL_FONT, VERT_DIR, 4);
          setcolor(14);
             outtextxy(x2,245,abc);
             aa1 = aa1 + aa2;
             a1 = a1 + a;
     }
}
     for(i=0; i<nn; i++) data[i] *= -1;
}

/* function to plot a box on the screen */ box()
{
     setgraphmode(cmode);
     lowvideo(); setcolor(3);
     rectangle(30,20,410,90);
     rectangle(32,22,408,88);
}
box1()
{
     setgraphmode(cmode);
     lowvideo(); setcolor(3);
     rectangle(30,20,410,190);
```

```
        rectangle(32,22,408,188);
}

/* function to check the status of spawn */ status(int val)
{
    if(val== -1)
        printf("Failed to start child process\n");
    else if(val > 0)
        printf("Child process terminated abnormally\n");
}

/* function to do analytical signal magnitude on the given
   signal data
*/ asig(float data[])
{
    int i,j,k;
    int nn, isign, npt;
    float temp[2048] = {0};
    npt = 2 * npts; nn = npt / 2; k = 0;
    for(i=0; i<npt; i+=2)
    {
        j = i + 1;
        temp[i] = data[k];

temp[j] = 0.0;
        k = k + 1;
    } isign = 1;
    four(temp, nn, isign);

for(i=0; i<npt; i++)
    {
        if(i < nn) temp[i] = 0.0;
    }
    isign = -1;
    four(temp, nn, isign);
    for(i=0; i<npt; i++) temp[i] = temp[i]/nn;

k=0;
    for(i=0;i<npt-1; i+=2)
    {
        j = i + 1;
        data[k] = sqrt(pow(temp[i],2) + pow(temp[j],2));
        k = k + 1;
    }
}

/* function to perform fft on the data */ four(float temp[], int nn, int isign)
{
```

```c
double wr, wi, wpr, wpi, wtemp, theta;
float tempr, tempi;
int n, j, i, mmax, istep, m;

n = 2 * nn; j = 1;
for(i=1; i<=n; i+=2)
{
if(j > i)
    {
       tempr = temp[j];
       tempi = temp[j+1];
       temp[j] = temp[i];
       temp[j+1] = temp[i+1];
       temp[i] = tempr;
       temp[i+1] = tempi;
    }
m = n/2;
while(m >= 2 && j > m)
        {
                j = j - m;
                m = m/2;
        }
    j = j + m;
}
    mmax = 2;
    while(n > mmax)
        {
                istep = 2 * mmax;
                theta = 6.28318530717959 / (isign * mmax);
                wpr = -2.0 * pow(sin(0.5*theta),2);
                wpi = sin(theta); wr = 1.0; wi = 0.0;
                for(m=1; m<=mmax; m+=2)
                {
                        for(i=m; i<=n; i+=istep)
                        {
                                j = i + mmax;
    tempr = wr * temp[j] - wi * temp[j+1];
    tempi = wr * temp[j+1] + wi * temp[j];
    temp[j] = temp[i] - tempr;
    temp[j+1] = temp[i+1] - tempi;
    temp[i] = temp[i] + tempr;
    temp[i+1] = temp[i+1] + tempi;
                        }
                        wtemp = wr;
                        wr = wr * wpr - wi * wpi + wr;
                        wi = wi * wpr + wtemp * wpi + wi;
                }
            mmax = istep;
            }
}

/* function to perform a time delay calculation
   based on the analytical signal
*/
```

```
func_tim(float data[])
{
    int imax, imin;
    float max=-1;
    float min;
    double td1, td2;
    for(i=0; i<npts; i++)
    {
        if(data[i] > max)
        {
            max = data[i];
            imax = i;
        }
    } kk=imax; min=data[imax];
    for(i=imax+1; i<imax+24; i++)
    {
        if(data[i] < min)
        {
            min = data[i];
            imin = i;
            if(data[i+1] > min)
                j=imin+1;
        }
    }
        td1=(data[kk-1]-data[kk+1]);
        td1=td1/(data[kk-1]-2*data[kk]+data[kk+1]);
        td2=(data[j-1]-data[j+1]);
        td2=td2/(data[j-1]-2*data[j]+data[j+1]);
        fract=(td2*0.5+j)-(td1*0.5+kk);
    return(kk,j,fract);
}

/* include file scan.h containing program definitions */ include "menu.h"
include <math.h>
#include <stdio.h>
#include <conio.h>
#include <stdlib.h>
#include <process.h>
#include <camac_c.h>
include <graphics.h> int N, F, A, Q, X, DT;
int cn, ndel, npts, nrec, cmode;
int avg, i, j, k, mm, kk, row, col;
float fract;

char name[11], abc[5], name1[11], name2[11];
char *pathname = "C:\\RAM\\FPROG\\FIB.EXE";
char *path = "C:\\RAM\\CPROG\\BRIDGE.EXE";
char *path1 = "C:\\RAM\\CPROG\\MOTOR.EXE";
```

```c
char *args[] = { "FIB.EXE", "BRIDGE.EXE", "MOTOR.EXE", "2nd",
NULL };

FILE *fp, *fpp;

struct ITEM mnuMain[] =
{                  /* Highlight  Char  Pos */
    0, "Camac Parameters",  /* C     0 */
    0, "Digitize",          /* D     0 */

0, "Plot",              /* P     0 */
    0, "Sig Magnitude",     /* S     0 */
    0, "Write",             /* W     0 */
    0, "Time Delay",        /* T     0 */
    9, "Shell to Fib",      /* F     9 */
    9, "Shell to Bridge",   /* B     9 */
    9, "Shell to Motor",    /* M     9 */
    0, "Quit",              /* Q     0 */
    0, NULL
};

struct ITEM mnuCam[]=
{
    8, "Channel 2",         /* 2     8 */
    8, "Channel 7",         /* 7     8 */
    0, "Both Channels",     /* B     0 */
    0, "Window Offset",     /* W     0 */
    8, "Window Range",      /* R     8 */
    8, "Record Length",     /* C     2 */
    0, "# Average",         /* #     0 */
    1, "Plot Scale",        /* L     1 */
    0, "Previous Menu",     /* P     0 */
};

enum SE
{
    KMAC, DIG, PLO, SIG, WR, TIM, FIB, BR, MOT, QUIT
};
enum SEL
{
    CHA, CHN, BOT, WIO, WIR, RL, AV, PS, EX
};

/*
Declarations of CAMAC I/O routines for inclusion in
a C program.   Uses C parameter passing convention.
*/
void far Crate_set (int far * /* crate nbr */);
void far Camo (int far *,int far *,int far *,/*N,A,F */
    int far *,int far *,int far *);    /* D,Q,X */
void far Cami (int far *,int far *,int far *, /* N,A,F */
    int far *,int far *,int far *);    /* D,Q,X */
void far Camo24 (int far *,int far *,int far *,/* N,A,F */
    int far *,int far *,int far *);    /* D,Q,X */
```

```c
void far Cami24 (int far *,int far *,int far *,/* N,A,F */
    int far *,int far *,int far *);     /* D,Q,X */
void far Caml (int far * /* Lam number */);
void far Camcl (int far * /* Control_word */);

void far Dmaset (int far *,int far *,int far *,int far *);
     /* crate,     nbytes,    qmode,    error */
void far Dmai (int far *,int far *,int far *,/* N,A,F */
    int far *,int far *);               /* Data,Error */
void far Dmao (int far *,int far *,int far *,/* N,A,F */
    int far *,int far *);               /* Data,Error */
void far Camcyc (int far * /* nbytes */);
```

```
/* Sub program menu, for creating popup menus */

/* MENU - Module of functions to put menus on the screen and
handle keyboard input. To use it, include the MENU.H file in
your program. The following functions are public:
Menu       -   Puts a menu on screen and reads input for it
getkey     -   Gets ASCII or function key
outchar    -   Displays character using current text position
and color
The following structures are defined:
MENU       -   Defines menu colors, box type, and centering
ITEM       -   Defines text of menu item and index of
highlight character
The global variable "mnuAtrib" has type MENU. Change this
variable to change menu appearance.
 */
```

```c
#include <string.h>
#include <stdio.h>
#include <stddef.h>
#include <ctype.h>
#include <graphics.h>
#include <bios.h>
#include "menu.h" /* file definitions */
```

```
/* Default menu attribute. The default works for color or B&W.
You can override the default value by defining your own MENU
variable and assigning it to mnuAtrib, or you can modify
specific fields at run time. For example, you could use a
different attribute for color than for black and white.
 */
struct MENU mnuAtrib =
{
    _TWHITE,    _TWHITE,     _TBRIGHTWHITE,   _TLIGHTYELLOW,
_TLIGHTRED, _TBLACK, _TBLACK,  _TWHITE,    _TBLACK,  _TWHITE
};
```

```
/* Menu - Puts menu on screen and reads menu input from
keyboard. When a highlighted hot key or ENTER is pressed,
returns the index of the selected menu item.
```

```
Params: row and col - If "fCentered" attribute of "mnuAtrib"
is true, center row and column of menu; otherwise top left of
menu
aItem - array of structure containing the text of each item
and the index of the highlighted hot key
iCur - index of the current selection--pass 0 for first item,
or maintain a static value
Return: The index of the selected item
Uses:   mnuAtrib
*/ int Menu( int x, int y, struct ITEM aItem[], int iCur )
{
int cItem,cchItem = 2;   /* Counts of items and chars per
                            item       */
int i, iPrev;            /* Indexes - temporary and previous
                            */
int acchItem[MAXITEM];   /* Array of counts of character in
                            items      */
char *pchT;              /* Temporary character pointer */
char achHilite[36];      /* Array for highlight characters */
int  uKey;               /* Key code  */
long bgColor;            /* Screen color */
short fgColor;
int oldx, oldy;          /* Screen position */
int polygon[10];         /* Rectangle to fill an area on the
                            screen     */

/* Save screen information. */
    bgColor = getbkcolor();
    fgColor = getcolor();
    oldx    = getx();
    oldy    = gety();

/* Count items, find longest, and put count of each in array.
Also, put the highlighted character from each in a string.
*/
    for( cItem = 0; aItem[cItem].achItem[0]; cItem++ )
    {
        acchItem[cItem] = strlen( aItem[cItem].achItem );
        cchItem = (acchItem[cItem] > cchItem) ?
                   acchItem[cItem] : cchItem;
        i = aItem[cItem].iHilite;
        achHilite[cItem] = aItem[cItem].achItem[i];
    }
    cchItem += 2;
    achHilite[cItem] = 0;     /* Null-terminate and
                                 lowercase string */
    strlwr( achHilite );

setviewport( x, y, x+cchItem*9, y + cItem*17, 1);
    setcolor( CYAN );
    setfillstyle( SOLID_FILL, BLUE );
    polygon[0] = polygon[2] = polygon[8] = 0; /* x */
    polygon[1] = polygon[7] = polygon[9] = 0; /* y */
```

```
        polygon[3] = polygon[5] = cItem * 17;
        polygon[4] = polygon[6] = cchItem * 9;
        fillpoly( 5, polygon);

rectangle( 1, 1, cchItem*9-1, cItem*17-1 );

/* Put items on menu. */
        for( i = 0; i < cItem; i++ )
        {
    if( i == iCur )
    Itemize( i*16+8, 8, TRUE, aItem[i], cchItem - acchItem[i]);
    else
    Itemize( i*16+8, 8, FALSE, aItem[i], cchItem - acchItem[i]);
        } while( TRUE )
        {
        /* Wait until a uKey is pressed, then evaluate it. */
            uKey = getkey();
            switch( uKey )
            {
                case U_UP:                      /* Up key      */
                    iPrev = iCur;
            iCur = (iCur > 0) ? (--iCur % cItem) : cItem - 1;
                    break;
                case U_DN:                      /* Down key    */
                    iPrev = iCur;
            iCur = (iCur < cItem) ? (++iCur % cItem) : 0;
                    break;
                default:
                    if( uKey > 256 )    /* Ignore unknown
                                            function key */
                        continue;
                    pchT = strchr( achHilite, tolower( uKey ) );
                    if( pchT != NULL )   /* If in highlight
                                                string,      */
                    iCur = pchT - achHilite; /* evaluate and
                                                fall through */
                    else {
                        putchar( '\a' );
                        continue;           /* Ignore unknown
                                                ASCII key    */
                    }
                case ENTER:
                    setbkcolor( bgColor );
                    setcolor( fgColor );
                    moveto( oldx, oldy);
                    return iCur;
            }

/* Redisplay current and previous. */

Itemize(  iCur*16+8,  8,TRUE,  aItem[iCur],  cchItem -
    acchItem[iCur] );
    Itemize(  iPrev*16+8,  8,FALSE, aItem[iPrev], cchItem -
```

```
acchItem[iPrev] );
    }
}

/* Itemize - Display one selection (item) of a menu. This
function is normally only used internally by Menu.
Params: row and col - top left of menu
fCur - flag set if item is current selection
itm - structure containing item text and index of highlight
cBlank - count of blanks to fill
Return: none
Uses:   mnuAtrib
*/ void Itemize( int y, int x, int fCur, struct ITEM itm, int
cBlank )
{
    int i;
    char achT[MAXITEM];                 /* Temporary array of
characters */
    static int polygon[10];             /* Rectangle to fill an
area on the screen */

/* Set text position and color. */
    moveto(x, y);
    if( fCur )
         setcolor( mnuAtrib.fgSelect );
    else
        setcolor  ( mnuAtrib.fgNormal );
    /* Display item and fill blanks. */
    strcat( strcpy( achT, " " ), itm.achItem );
    outtext( achT );
    memset( achT, ' ', cBlank-- );
    achT[cBlank] = 0;
    outtext( achT );

/* Set position and color of highlight character, then
display it. */
    i = itm.iHilite;
    moveto( x + 8*(i+1), y );
    if( fCur )

setcolor  ( mnuAtrib.fgSelHilite );
    else
        setcolor  ( mnuAtrib.fgNormHilite );
    outchar( itm.achItem[i] );
} int getkey(void)

/* Uses the BIOS to read the next keyboard character */
{
 int key, lo, hi;

key = bioskey(0);
 lo = key & 0X00FF;
```

```c
    hi = (key & 0XFF00) >> 8;
    return((lo == 0) ? hi + 256 : lo);
}
/* getkey */

/* _outchar - Display a character. This is the character
equivalent of _outtext. It is affected by _settextposition,
_settextcolor, and _setbkcolor. It should not be used in
loops. Build strings and then _outtext to show multiple
characters.
Params: out - character to be displayed
Return: none
*/
void outchar( char out )
{
    static char achT[2] = " ";        /* Temporary array of
                                         characters */ achT[0] = out;
    outtext( achT );
}

/* include file menu.h containing file definitions for menu.c
*/ define TRUE  1
define FALSE 0

/* Sample key codes for getkey. Additional codes in the same
format may be added.
*/ define U_UP    0x0148      /* Unshifted */
define U_DN    0x0150
#define U_LT    0x014b
#define U_RT    0x014d
#define S_UP    0x0248      /* Shifted */
#define S_DN    0x0250
#define S_LT    0x024b
define S_RT    0x024d define N_PLUS   0x014e     /* PLUS and MINUS on numeric
keypad */
define N_MINUS  0x014a define ENTER     13        /* ASCII */
define ESC       0x1b
#define BACKSPACE 0x8
```

/* Text output colors. Note that monochrome can only use
_TBLACK, _TWHITE, _TBRIGHTWHITE, and _TUNDERLINE. Graphics
black-and-white
can only use the first three of these. The first eight colors
can be used as background colors (although they may need to
be cast to long).
*/

```c
enum TEXTCOLORS
{
    _TBLACK,        _TBLUE,         _TGREEN,        _TCYAN,
    _TRED,          _TMAGENTA,      _TBROWN,        _TWHITE,
    _TGREY,         _TLIGHTBLUE,    _TLIGHTGREEN,
    _TLIGHTCYAN,    _TLIGHTRED,     _TLIGHTMAGENTA,
    _TLIGHTYELLOW,  _TBRIGHTWHITE,
};

#define _TUNDERLINE 1

/* Structure and global variable for menu attributes */ struct MENU
{
    int     fgBorder, fgNormal, fgSelect, fgNormHilite,
            fgSelHilite;
    long    bgBorder, bgNormal, bgSelect, bgNormHilite,
            bgSelHilite;
};

extern struct MENU mnuAtrib;

/* Structure and maximum length for menu items */ define MAXITEM 20
struct ITEM
{
    int     iHilite;
    char    achItem[MAXITEM];
};
/* Public menu, output, and input functions */
int Menu( int row, int col, struct ITEM aItem[], int iCur );
void Box( int row, int col, int rowLast, int colLast );
void Itemize( int row, int col, int fCur, struct ITEM itm, int cBlank );
int GetKey( void );
void outchar( char out );
```

```
*      This program computes the fiber volume fraction and
*        porosity of a prepreg based on the ultrasonic velocity
*        measurements.The material properties of the fiber
*        and matrix are required as input. This program uses a
*        non linear equation solver dneqnf developed by IMSL.
*
       program fib
       implicit double precision (a-h,o-z)
       real*8 KfTT,km,mden,Num,NufLT
       dimension xin(2), x(2)
       character infile(2)*12
       common /a/ mden,km,Gm,fden,KfTT,GfTT,GfLT,EfL,NufLT
       common /vel/ cl, sl
       parameter(errrel = 1.d-12)
       parameter(itmax = 10000)
       external fcn
```

```fortran
*
*     Input Material Properties Of Matrix
*
5     print*, 'Enter Matrix data file :'
      read(*,30)infile(1)
      open(121,file=infile(1))
      read(121,*)mden
      read(121,*)Em
      read(121,*)Num
      close(121)
*
*     Input Material Properties Of Fiber
*
      print *,'Enter Fiber data file :'
      read(*,30)infile(2)
      open(122,file=infile(2))
      read(122,*)fden
      read(122,*)EfL
      read(122,*)NufLT
      read(122,*)GfLT
      read(122,*)GfTT
      read(122,*)KfTT
      close(122)
*
*     Input The Measured Velocities
*
7     print *,'Lv, Sv :'
      read *,cl,sl
*
*     Allocate Initial Guesses
*
      n=2
      xin(1) = 0.d0
      xin(2) = 0.5d0
*
*     Call Non Linear Equation Solver
*
      call dneqnf(fcn, errrel, n, itmax, xin, x, fnorm)
*
      print 22,x(1)*100.d0
      print 24,x(2)*100.d0
      orc = (1.d0 - x(2))*x(1)*100.d0
      print 26,orc
      print 28
      read *,ans
      if(ans .eq. 1)go to 7
      if(ans .eq. 2)go to 5
22    format(1x,'Resin void content    (%)   : ',f6.2)
24    format(1x,'Fiber volume fraction (%)   : ',f6.2)
26    format(1x,'Overall void content  (%)   : ',f6.2)
28    format(1x,'0 - Stop, 1 - Run another test, 2 - Change
     properties')
      end subroutine fcn(x,f,n)
      implicit double precision (a-h,o-z)
```

```fortran
      dimension c(6,6),x(n),f(n)
      real*8 KfTT,k,km,kmm,mden,Numm,NufLT,Nua
      real*8 mmd,mf,mmf
      common /a/ mden,km,Gm,fden,KfTT,GfTT,GfLT,EfL,NufLT
      common /vel/ cl,sl
*
*     Calculate Modified Matrix Properties
*
      if(x(1) .lt. 0.d0)x(1) = 0.d0
      ff = x(2)
      vf = x(1)
      mf = 1.d0 - ff
      mmf = 1.d0 - vf
      mmd = mmf*mden
      Gs = Gm*(9.d0*km + 8.d0*Gm)/(6.d0*(km + 2.d0*Gm))
      Kmm = km*(1.d0 - vf/(1.d0 - km/(km + 4.d0*Gm/3.d0)))
      Gmm = Gm*(1.d0 - vf/(1.d0 - Gm/(Gm + Gs)))
      Emm = 9.d0*Gmm*kmm/(3.d0*kmm + Gmm)
      Numm = (3.d0*kmm - 2.d0*Gmm)/(6.d0*kmm + 2.d0*Gmm)
      Kmm = Kmm + Gmm/3.d0
*
*     Calculate Engineering Constants
*
      den = mmd + ff*(fden - mmd)
      k = Kmm + ff/(1.d0/(KfTT - Kmm) + mf/(Kmm + Gmm))
      temp1 = mf/KfTT + ff/Kmm + 1.d0/Gmm
      temp2 = NufLT - Numm
      Ea = EfL*ff + Emm*mf + 4.d0*mf*ff*temp2**2/temp1
      Nua = Numm*mf+ NufLT*ff-temp2* (1.d0/KfTT-1.d0/Kmm)*
     #       ff*mf/temp1
      Ga = Gmm + ff/(1.d0/(GfLT - Gmm) + mf/(2.d0*Gmm))
      Gt = Gmm + ff/(1.d0/(GfLT - Gmm) +
     #       mf/(2.d0*Gmm)*(Kmm+2*Gmm)/(Kmm+Gmm))
*
*     Calculate Laminae Stiffness
*
      c(1,1) = k + Gt
      c(1,2) = k - Gt
      c(1,3) = 2.d0*Nua*k
      c(2,2) = c(1,1)
      c(2,3) = c(1,3)
      c(3,3) = Ea + 4.d0*k*Nua**2
      c(4,4) = Ga
      c(5,5) = c(4,4)
      c(6,6) = Gt
*
*     Calculate Longitudinal And Shear Velocity
*
      if(c(2,2) .lt. 0.d0)c(2,2)=0.d0
      vl = dsqrt(c(2,2)/den)
      if(c(6,6) .lt. 0.d0)c(6,6)=0.d0
      vs = dsqrt(c(6,6)/den)
*
*     Function To Best Fit The Fiber Vol Frac And Porosity
*
```

```
f(1) = vl - cl
f(2) = vs - sl
return
end
```

TABLE II

```
*    This program computes the fiber volume fraction and
*     porosity of a prepreg based on the ultrasonic velocity
*     measurements.The material properties of the fiber
*     and matrix are required as input. This program uses a
*     non linear equation solver dneqnf developed by IMSL.
*
      program fib
      implicit double precision (a-h,o-z)
      real*8 KfTT,km,mden,Num,NufLT
      dimension xin(2), x(2)
      character infile(2)*12
      common /a/ mden,km,Gm,fden,KfTT,GfTT,GfLT,EfL,NufLT
      common /vel/ cl, sl
      parameter(errrel = 1.d-12)
      parameter(itmax = 10000)
      external fcn
*
*     Input Material Properties Of Matrix
*
5     print*, 'Enter Matrix data file :'
      read(*,30)infile(1)
      open(121,file=infile(1))
      read(121,*)mden
      read(121,*)Em
      read(121,*)Num
      close(121)
*
*     Input Material Properties Of Fiber
*
      print *,'Enter Fiber data file :'
      read(*,30)infile(2)
      open(122,file=infile(2))
      read(122,*)fden
      read(122,*)EfL
      read(122,*)NufLT
      read(122,*)GfLT
      read(122,*)GfTT
      read(122,*)KfTT
      close(122)
*
*     Input The Measured Velocities
*
```

```
7       print *,'Lv, Sv :'
        read *,cl,sl
*
*       Allocate Initial Guesses
*
        n=2
        xin(1) = 0.d0
        xin(2) = 0.5d0
*
*       Call Non Linear Equation Solver
*
        call dneqnf(fcn, errrel, n, itmax, xin, x, fnorm)

print 22,x(1)*100.d0
        print 24,x(2)*100.d0
        orc = (1.d0 - x(2))*x(1)*100.d0
        print 26,orc
        print 28
        read *,ans
        if(ans .eq. 1)go to 7
        if(ans .eq. 2)go to 5
22      format(1x,'Resin void content      (%)   : ',f6.2)
24      format(1x,'Fiber volume fraction  (%)   : ',f6.2)
26      format(1x,'Overall void content   (%)   : ',f6.2)
28      format(1x,'0 - Stop, 1 - Run another test, 2 - Change
        properties')
        end subroutine fcn(x,f,n)
        implicit double precision (a-h,o-z)
        dimension c(6,6),x(n),f(n)
        real*8 KfTT,k,km,kmm,mden,Numm,NufLT,Nua
        real*8 mmd,mf,mmf
        common /a/ mden,km,Gm,fden,KfTT,GfTT,GfLT,EfL,NufLT
        common /vel/ cl,sl
*
*       Calculate Modified Matrix Properties
*
        if(x(1) .lt. 0.d0)x(1) = 0.d0
        ff = x(2)
        vf = x(1)
        mf = 1.d0 - ff
        mmf = 1.d0 - vf
        mmd = mmf*mden
        Gs  = Gm*(9.d0*km + 8.d0*Gm)/(6.d0*(km + 2.d0*Gm))
        Kmm = km*(1.d0 - vf/(1.d0 - km/(km + 4.d0*Gm/3.d0)))
        Gmm = Gm*(1.d0 - vf/(1.d0 - Gm/(Gm + Gs)))
        Emm = 9.d0*Gmm*kmm/(3.d0*kmm + Gmm)

Numm = (3.d0*kmm - 2.d0*Gmm)/(6.d0*kmm + 2.d0*Gmm)
        Kmm  = Kmm + Gmm/3.d0
*
*       Calculate Engineering Constants
*
        den = mmd + ff*(fden - mmd)
        k = Kmm + ff/(1.d0/(KfTT - Kmm) + mf/(Kmm + Gmm))
```

```
temp1 = mf/KfTT + ff/Kmm + 1.d0/Gmm
temp2 = NufLT - Numm
Ea = EfL*ff + Emm*mf + 4.d0*mf*ff*temp2**2/temp1
Nua  = Numm*mf+ NufLT*ff-temp2* (1.d0/KfTT-1.d0/Kmm)*
#        ff*mf/temp1
Ga = Gmm + ff/(1.d0/(GfLT - Gmm) + mf/(2.d0*Gmm))
Gt = Gmm + ff/(1.d0/(GfLT - Gmm) +
#        mf/(2.d0*Gmm)*(Kmm+2*Gmm)/(Kmm+Gmm))
*
*  Calculate Laminae Stiffness
*
   c(1,1) = k + Gt
   c(1,2) = k - Gt
   c(1,3) = 2.d0*Nua*k
   c(2,2) = c(1,1)
   c(2,3) = c(1,3)
   c(3,3) = Ea + 4.d0*k*Nua**2
   c(4,4) = Ga
   c(5,5) = c(4,4)
   c(6,6) = Gt
*
*  Calculate Longitudinal And Shear Velocity
*
   if(c(2,2) .lt. 0.d0)c(2,2)=0.d0
   vl = dsqrt(c(2,2)/den)
   if(c(6,6) .lt. 0.d0)c(6,6)=0.d0
   vs = dsqrt(c(6,6)/den)
*
*  Function To Best Fit The Fiber Vol Frac And Porosity
*
   f(1) = vl - cl
   f(2) = vs - sl
   return
   end
```

What is claimed is:

1. An on-line method using a processor for non-destructively determining fiber volume fraction and resin porosity of a composite material wherein the following parameters of the composite material or prepreg are known: density, elastic modulii of the constituent materials and layup sequence, the method comprising:

supporting a transducer assembly above the composite material or prepreg;

moving the composite material or prepreg under the transducer assembly and periodically stopping the moving the composite material;

propagating two independent acoustic waves via the transducer assembly through the composite material each time the moving the composite material under the transducer assembly is stopped:

receiving the acoustic waves propagated through the composite material in the processor;

determining in the processor the velocity of each of the two acoustic waves propagated through the composite material from the received acoustic waves propagated through the composite material, the respective velocity being $V_1$ and $V_2$;

determining the thickness of the composite material and inputting the thickness into the processor; and determining in the processor the fiber volume fraction and resin porosity of the composite material using the velocities, $V_1$ and $V_2$, the thickness and the known parameters of density, the elastic modulii of the constituent materials and layup sequence.

2. The method of claim 1 wherein the step of moving the composite material further comprises:

supporting rotatingly a roller and a roller-transducer housing with the composite material being disposed between the roller and the roller-transducer housing whereby rotating the roller and the roller-transducer housing moves the composite material between the roller and the roller-transducer housing; and wherein the step of supporting the transducer assembly above the composite material further comprises:

supporting the transducer assembly in the roller-transducer housing in a fixed position whereby the transducer assembly is not rotated during the rotation of the roller and the roller-transducer housing; and wherein the step of moving the composite material under the transducer assembly further comprises:

rotating drivingly at least one of the roller and the roller-transducer housing for moving the composite material under the transducer assembly at a predetermined rate and periodically stopping the rotating of the roller and the roller-transducer housing for stopping the moving the composite material periodically.

3. The method of claim 2 wherein the step of moving the composite material further comprises stopping the moving of the composite material when the composite material has been moved a predetermined distance.

4. The method of claim 1 wherein the acoustic waves further defined as being ultrasonic waves.

5. Tho method of claim 2 wherein the step of propagating the two independent acoustic waves further comprises:
disposing water in the roller-transducer housing; and
propagating the two independent acoustic waves through the water, through the roller-transducer housing and through the composite material.

6. An on-line method using a processor for non-destructively determining fiber volume fraction and resin porosity of a composite material wherein the following parameters of the composite material or prepreg are known: density and layup sequence, the method comprising:
supporting a transducer assembly above the composite material or prepreg;
moving the composite material or prepreg under the transducer assembly and periodically stopping the moving the composite material;
determining the elastic modulii of the composite material;
propagating two independent acoustic waves via the transducer assembly via the transducer assembly through the composite material each time the moving the composite material under the transducer assembly is stopped;
receiving the acoustic waves propagated through the composite material in the processor;
determining in the processor the velocity of each of the two acoustic waves propagated through the composite material from the received acoustic waves propagated through the composite material, the respective velocity being $V_1$ and $V_2$;
determining the thickness of the composite material and inputting the thickness into the processor; and
determining in the processor the fiber volume fraction and resin porosity of the composite material using the velocities, $V_1$ and $V_2$, the thickness, the elastic modulii of the constituent materials and the known parameters of density and layup sequence.

7. The method of claim 6 wherein the step of moving the composite material further comprises:
supporting rotatingly a roller and a roller-transducer housing with the composite material being disposed between the roller and the roller-transducer housing whereby rotating the roller and the roller-transducer housing moves the composite material between the roller and the roller-transducer housing; and wherein the step of supporting the transducer assembly above the composite material further comprises:
supporting the transducer assembly in the roller-transducer housing in a fixed position whereby the transducer assembly is not rotated during the rotation of the roller and the roller-transducer housing; and wherein the step of moving the composite material under the transducer assembly further comprises:
rotating drivingly at least one of the roller and the roller-transducer housing for moving the composite material under the transducer assembly at a predetermined rate and periodically stopping the rotating of the roller and the roller-transducer housing for stopping the moving the composite material periodically.

8. The method of claim 7 wherein the step of moving the composite material further comprises stopping the moving of the composite material when the composite material has been moved a predetermined distance.

9. The method of claim 6 wherein the acoustic waves further defined as being ultrasonic waves.

10. The method of claim 7 wherein the step of propagating the two independent acoustic waves further comprises:
disposing water in the roller-transducer housing; and
propagating the two independent acoustic waves through the water, through the roller-transducer housing and through the composite material.

11. The method of claim 6 wherein the step of determining the elastic modulii comprises:
determining the dielectric constant of the composite material;
determining the elastic modulii of the composite material from the dielectric constant.

12. The method of claim 11 wherein the step of determining the elastic modulii from the determined dielectric constant is further defined as comprising:
providing sample composite materials, each sample composite material having material constituents substantially the same as the composite material to be tested and each sample composite material having a different state of cure;
determining the shear modulus and the Young's modulus and the dielectric constant of each of the sample composite materials to provide a correlation between the Young's modulus and the dielectric constant and the correlation between the shear modulus and the dielectric constant of each of the sample materials which comprises a state of cure data base;
determining the dielectric constant of the composite material to be tested; and
determining the elastic modulii comprising the shear modulus and the Young's modulus of the composite material to be tested using the measured dielectric constant of the composite material to be tested and the state of cure data base.

13. An apparatus for non-destructively determining fiber volume fraction and resin porosity of composite material comprising:
a roller having an outer peripheral surface;
a roller-transducer housing having an outer peripheral surface;
a support for rotatingly supporting the roller and the roller-transducer housing with outer peripheral surface of the roller being spaced a predetermined distance from the outer peripheral surface of the roller-transducer housing, the composite material being disposed between the outer peripheral surface of the roller and the outer peripheral surface of the roller-transducer housing whereby rotation of the roller and the roller-transducer housing moves the material in an advanced direction between the roller and the roller-transducer housing when the roller and the roller-transducer housing are rotating;

motor means for drivingly rotating at least one of the roller and the roller-transducer housing to move the composite material in the advanced direction;

a transducer assembly supported in the roller-transducer housing for propagating two acoustic waves through the composite material;

means for receiving the acoustic waves propagated through the composite material and outputting the received acoustic waves in a digital format; and a processor for receiving the two acoustic waves in a digital format and determining the velocity of each of the acoustic waves, $V_1$ and $V_2$, the processor having inputted therein a thickness of the composite material, a density, an elastic modulii of the constituents materials and a layup sequence, the processor determining the fiber volume fraction and the resin porosity of the composite material using the velocities, $V_1$ and $V_2$, the thickness of the composite material, the density, the elastic modulii of the constituent materials and the layup sequence.

14. The apparatus of claim 13 wherein the motor means is defined further as drivingly rotating at least one of the roller and the roller-transducer housing in response to a received signal, and periodically stopping the rotating of the roller and the roller-transducer housing for stopping the moving of the composite material in response to a received signal, and wherein the transducer assembly is defined further as propagating two acoustic waves through the composite material in response to a received signal each time the moving of the composite material is stopped, and wherein the processor is defined further as outputting a signal to the motor means for causing the motor means to drivingly rotate at least one of the roller and the roller-transducer housing to move the composite material in the advance direction, and outputting the signal to the motor means for periodically stopping the rotating of the roller and roller-transducer housing for stopping the moving the composite material, and wherein the transducer assembly is further defined as propagating the two acoustic waves through the composite material each time the moving of the composite material is stopped.

15. The apparatus of claim 13 wherein the support means further comprises:

a support;

a shaft secured to the support, the roller transducer housing being supported on the shaft; and means for rotatingly mounting the roller-transducer housing on the shaft; and wherein the roller-transducer housing further comprises a hollow portion formed in the roller-transducer housing, the transducer assembly being supported on the shaft and disposed in the hollow portion of the roller-transducer housing.

16. The apparatus of claim 15 wherein water is disposed in the hollow portion of the roller-transducer housing, the acoustic waves being propagated through the water, through a thickness of the roller-transducer housing and through the composite material.

* * * * *

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-identified patent and that said Letters Patent is hereby corrected as shown below:

Column 2, Line 67, please delete "$\sigma_{ij}=C_{ijk\ell k\ell}$" and substitute therefore --$\sqrt{\sigma_{ij}=C_{ijk\ell}\varepsilon_{k\ell}}$--.

Column 3, Line 45, please delete "$\sqrt{1313/\rho}$" and substitute therefore --$\sqrt{C_{1313/\rho}}$--.

Column 8, Line 27; after More, please delete "particular" and substitute therefore --particularly--.

Column 8, Line 29, after plate, please delete "61" and substitute therefore --60--.

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-identified patent and that said Letters Patent is hereby corrected as shown below:

Column 8, Line 36, after 16 is, please delete "support" and substitute --supported a--.

Column 28, Line 29, after Assuming, please delete "1" and substitute therefore --"$\ell$"--.

Column 28, Line 63; after tested, please delete "in" and substitute therefore --is--.

Column 29, Line 6; after positions, please delete "are" and substitute therefore --as--.

UNITED STATES PATENT AND TRADEMARK OFFICE
CERTIFICATE OF CORRECTION

PATENT NO. : 5,181,421

DATED : January 26, 1993

INVENTOR(S) : Ronald A. Kline

It is certified that error appears in the above-identified patent and that said Letters Patent is hereby corrected as shown below:

Column 29, Line 13, after dimensional, please delete "patters" and substitute therefore --patterns--.

Column 30, Line 49, after pair, please add --100 and 104--.

Column 30, Line 62; after processor, please add --26--.

Column 30, Line 64; after processor, please add --26--.

Column 31, Line 33, after 112, please delete "associate" and substitute therefore --associated--.

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-identified patent and that said Letters Patent is hereby corrected as shown below:

Column 31, Line 40, after material, please delete "10" and insert --106--.

Column 32, Line 2, please delete "ration" and substitute therefore --ratio--.

Column 33, Line 25, After 8-, please delete "17" and substitute therefore --18--.

Column 34, Line 47; after to, please add --be--.

Column 34, Line 62; please delete "$G_s = \dfrac{G_m(9K_m + 8G_m)}{G(K_m + 2G_m)}$ and substitute therefore --$G_s = \dfrac{G_m(9K_m + 8G_m)}{6(K_m + 2G_m)}$

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-identified patent and that said Letters Patent is hereby corrected as shown below:

Column 35, Line 32, after which, please delete "constitutes" and substitute therefore --consists--.

Column 35, Line 50, please delete $$K = K_m + \frac{V_f}{\frac{1}{K_f - K_m} + V_m K_m + G_m}$$

and substitute therefore $$K = K_m + \frac{V_f}{\frac{1}{K_f - K_m} + \frac{V_m}{K_m + G_m}}$$

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-identified patent and that said Letters Patent is hereby corrected as shown below:

Column 35, Line 63, in formula after $V_m$, please delete "$-V_f$" and substitute therefore --$V_f$--.

Column 36, Line 50, please delete formula "$C_{33} = E_a + 4Kv_a^2$" and substitute therefore the formula --$C_{33} = E_a + 4Kv_a^2$--.

Column 37, Line 21, please delete formula "$u_i = A_o a_i e^{i[k(lx)-wt]}_{tm(} 18)$" and substitute the following: --$u_i = A_o \alpha_i e^{i[k(l_i x_i) - \omega t]}$ (18)--.

Column 37, Line 25; please delete "$\alpha_1$" and substitute --$\alpha_i$--.

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-identified patent and that said Letters Patent is hereby corrected as shown below:

Column 37, Line 25, after direction, please delete "cosiness" and substitute therefore --cosines--.

Column 37, Line 27, after direction, please delete "cosiness" and substitute therefore --cosines--.

Column 37, Line 30, please delete "$x_1$" and substitute therefore --$x_i$--.

Column 39, Line 68; after signal, please insert --to be reflected from the prepreg--.

UNITED STATES PATENT AND TRADEMARK OFFICE
CERTIFICATE OF CORRECTION

PATENT NO. : 5,181,421
DATED : January 26, 1993
INVENTOR(S) : Ronald A. Kline

It is certified that error appears in the above-indentified patent and that said Letters Patent is hereby corrected as shown below:

Column 40, Line 9, please delete formula "$\dfrac{2 L_2}{V_x}$" and substitute therefore --$\dfrac{2 L_2}{V_c}$--.

Column 44, Line 35, after rev/sec$^2$, please insert --.--.

Column 44, Line 51, after distance, please delete "324" and substitute therefore --334--.

Column 91, Line 12, please delete "Tho" and substitute therefore --The--.

Signed and Sealed this

Eighth Day of March, 1994

BRUCE LEHMAN

Attest:

Attesting Officer

Commissioner of Patents and Trademarks